United States Patent
Bagwell et al.

(10) Patent No.: US 10,070,880 B2
(45) Date of Patent: Sep. 11, 2018

(54) MINIATURE DEVICE PLATFORM FOR NAVIGATION ON MOVING ORGANS

(71) Applicant: Actuated Medical, Inc., Bellefonte, PA (US)

(72) Inventors: Roger B Bagwell, Bellefonte, PA (US); Brian Matthew Park, Bellefonte, PA (US); Casey A Scruggs, Middleburg, PA (US); Kevin A Snook, State College, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 571 days.

(21) Appl. No.: 14/251,615

(22) Filed: Apr. 13, 2014

(65) Prior Publication Data

US 2014/0309683 A1    Oct. 16, 2014

Related U.S. Application Data

(60) Provisional application No. 61/811,956, filed on Apr. 15, 2013, provisional application No. 61/937,912, filed on Feb. 10, 2014.

(51) Int. Cl.
| | |
|---|---|
| *A61B 18/14* | (2006.01) |
| *A61B 17/32* | (2006.01) |
| *A61B 17/29* | (2006.01) |
| *A61B 17/22* | (2006.01) |
| *A61B 1/00* | (2006.01) |
| *A61B 18/00* | (2006.01) |

(52) U.S. Cl.
CPC ........ *A61B 17/29* (2013.01); *A61B 17/22031* (2013.01); *A61B 18/1492* (2013.01);
(Continued)

(58) Field of Classification Search
CPC .... A61B 2017/2926; A61B 2018/1405; A61B 18/1442; A61B 2017/32004; A61B 2017/320758; A61B 2017/320766; A61B 2017/320775; A61B 2017/2946

(56) References Cited

U.S. PATENT DOCUMENTS 5,549,627 A * 8/1996 Kieturakis ............. A61B 17/29
606/206
5,766,215 A * 6/1998 Muri .................... A61B 18/149
606/41

(Continued)

OTHER PUBLICATIONS

International Searching Authority; International Search Report and Written Opinion of the International Searching Authority; International Application No. PCT/US2014/34017; Patent Cooperation Treaty;.pp. 1-16; publisher United States International Searching Authority; Published Alexandria, Virginia, US; copyright and dated Jun. 1, 2015; copy enclosed (16 pages).

*Primary Examiner* — Ronald Hupczey, Jr.
*Assistant Examiner* — Bo Ouyang
(74) *Attorney, Agent, or Firm* — Metz Lewis Brodman Must O'Keefe LLC

(57) ABSTRACT

A device for gripping tissue that is inside of a patient for use in delivering therapy is provided. The device may include a first gear that rotates and that engages the tissue. A second gear that also rotates may be included and may likewise engage the tissue. A spacing mechanism may be included in the device that adjusts the spacing between the first and second gears such that the first and second gears are moved closer to one another and moved farther from one another.

38 Claims, 26 Drawing Sheets

(52) U.S. Cl.
CPC ......... *A61B 1/0014* (2013.01); *A61B 1/00087* (2013.01); *A61B 2017/2943* (2013.01); *A61B 2017/2947* (2013.01); *A61B 2018/00208* (2013.01); *A61B 2018/00291* (2013.01); *A61B 2018/1405* (2013.01); *A61B 2218/002* (2013.01); *A61B 2218/007* (2013.01)

(58) Field of Classification Search
USPC .................................................. 606/127, 113
See application file for complete search history.

(56) References Cited

U.S. PATENT DOCUMENTS

| | | | |
|---|---|---|---|
| 8,100,900 B2* | 1/2012 | Prinz .................... | A61B 18/18 606/20 |
| 2005/0256524 A1* | 11/2005 | Long .................. | A61B 18/1492 606/41 |
| 2008/0221504 A1 | 9/2008 | Aghion | |
| 2009/0281534 A1 | 11/2009 | Prinz | |
| 2009/0306541 A1* | 12/2009 | Kano .................. | A61B 10/0266 600/564 |
| 2010/0010492 A1* | 1/2010 | Lockard ............... | A61B 17/221 606/79 |
| 2011/0087266 A1* | 4/2011 | Conlon .................. | A61B 17/29 606/205 |
| 2011/0270241 A1* | 11/2011 | Boutoussov ....... | A61B 1/00163 606/33 |
| 2012/0022532 A1* | 1/2012 | Garrison ................ | A61B 18/14 606/52 |
| 2012/0035606 A1 | 2/2012 | Kano | |
| 2013/0012975 A1* | 1/2013 | Schmitz ................. | A61B 17/16 606/179 |

* cited by examiner

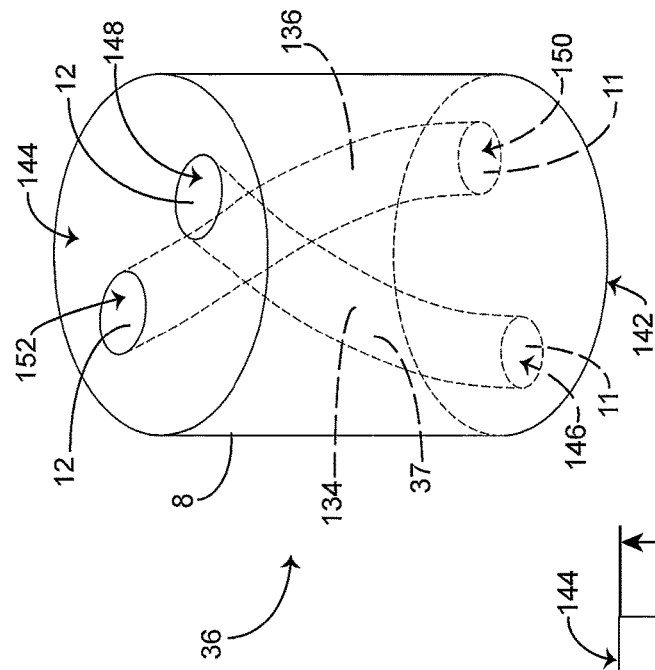
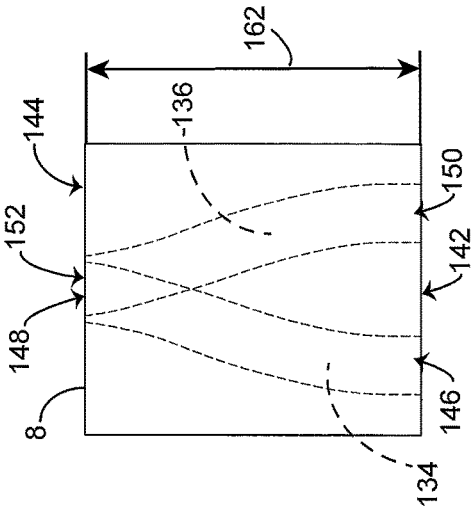
FIG. 4A
FIG. 4D
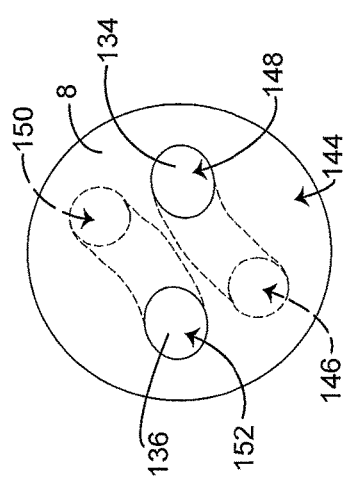
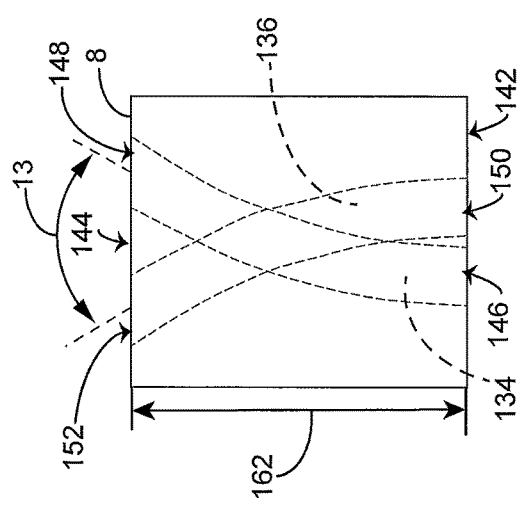
FIG. 4B
FIG. 4C $$x_c(h) = \frac{x_t + x_b}{ln(|cos(-\gamma)|)} \cdot ln\left(\left|cos\left(-\frac{h}{h_t}\gamma\right)\right|\right) - x_b$$

$$y_c(h) = -W(h) \cdot \frac{y_b}{2} \cdot \left[cos\left(\frac{\pi h}{h_t}\right) + 1\right]$$

where:

$x_c(h)$ = center x-coordinate equation for nested slide path
$y_c(h)$ = center y-coordinate equation for nested slide path
$x_t$ = x-offset at top of slide (distal end)
$x_b$ = x-offset at bottom of slide (proximal end)
$y_b$ = y-offset at bottom of slide (proximal end)
$h_t$ = height of slide
$W(h)$ = weighting factor for shaping curvature (very small < 0.05)
$\gamma$ = exit angle of tubes.

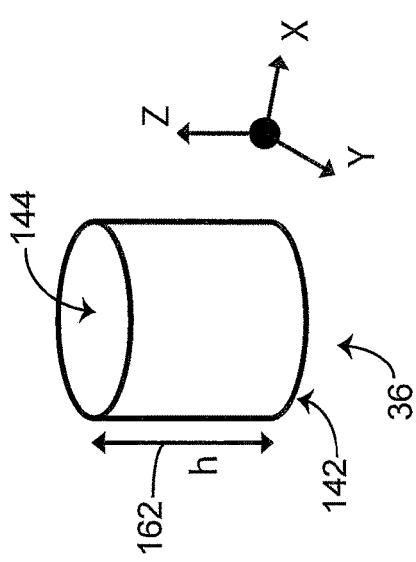

FIG. 5

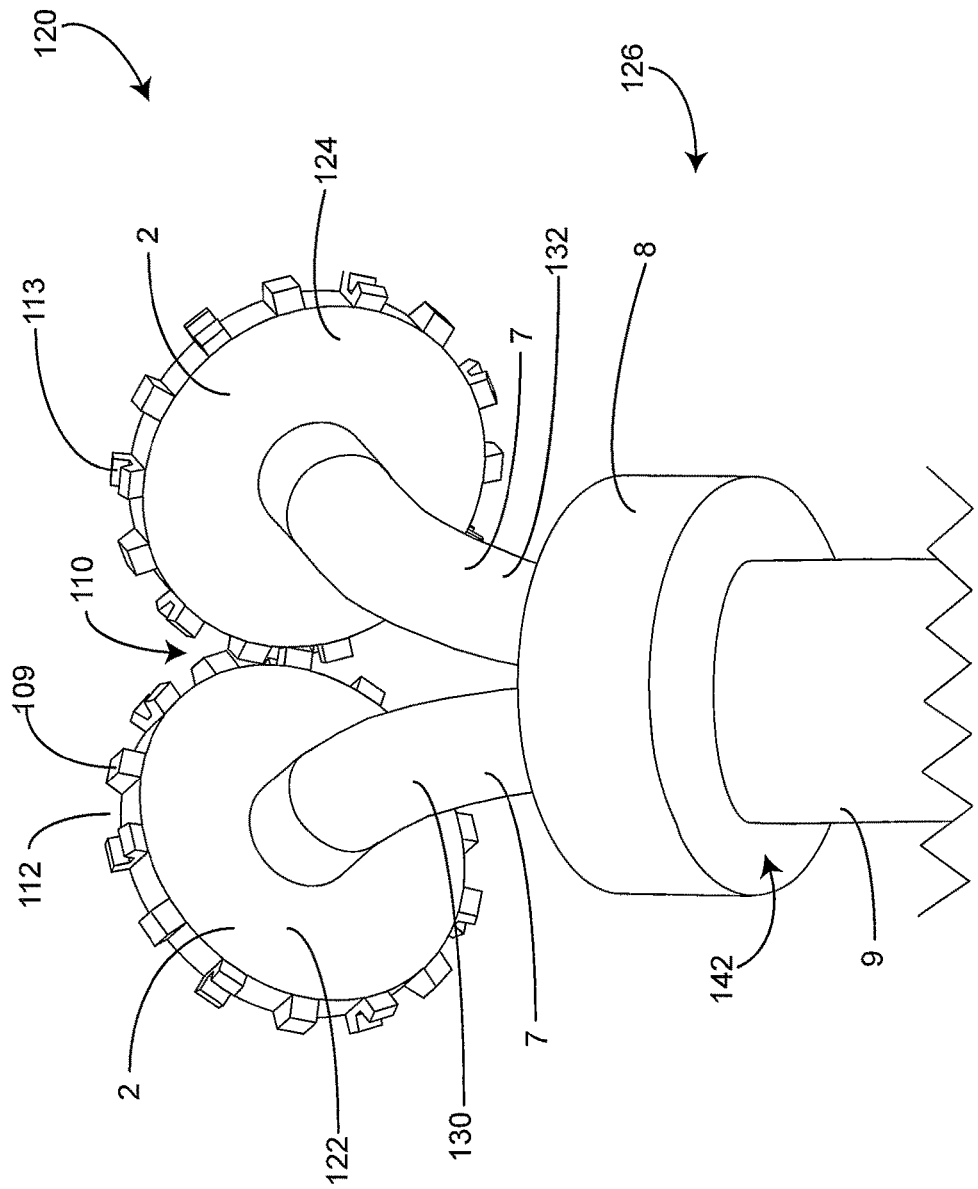

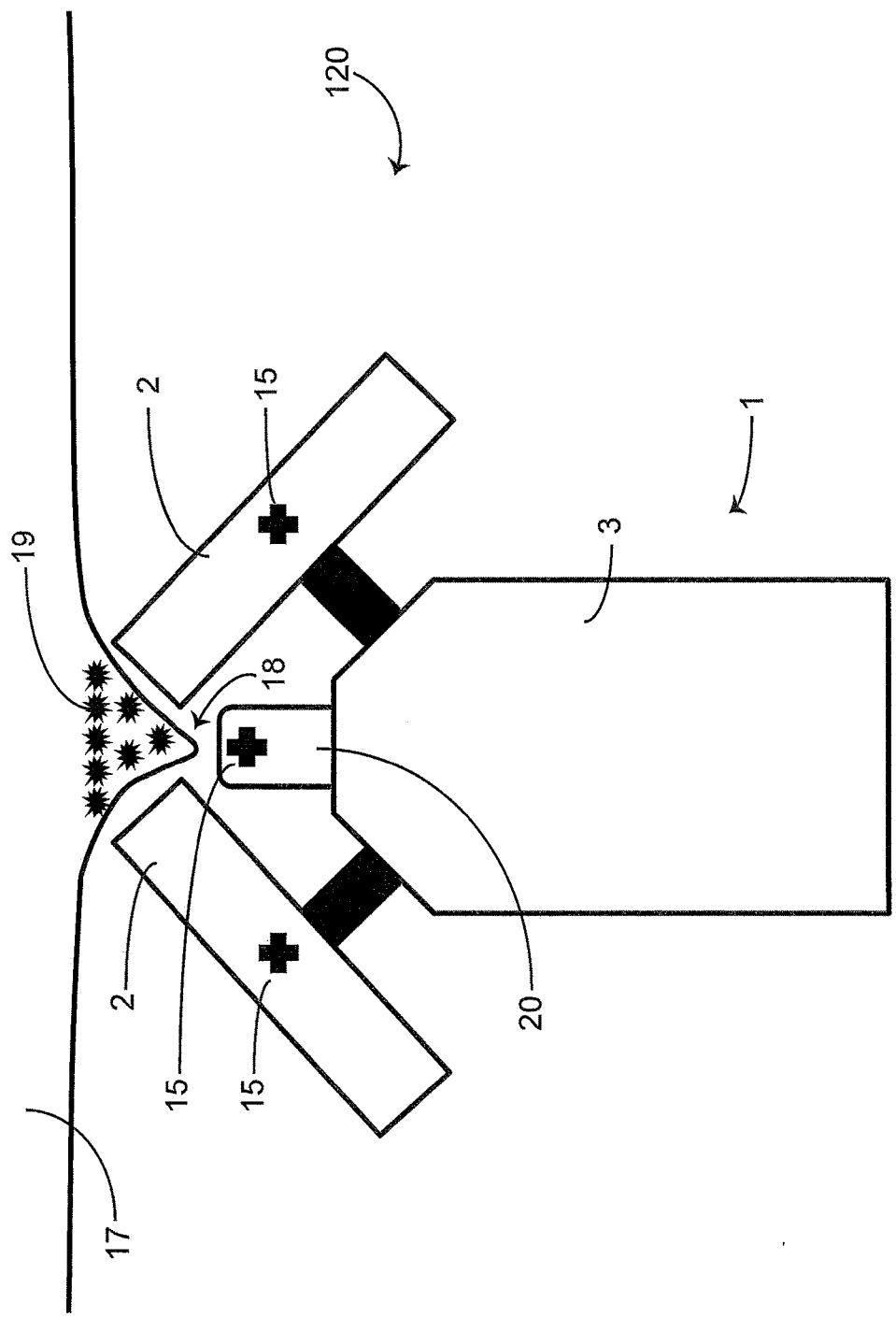

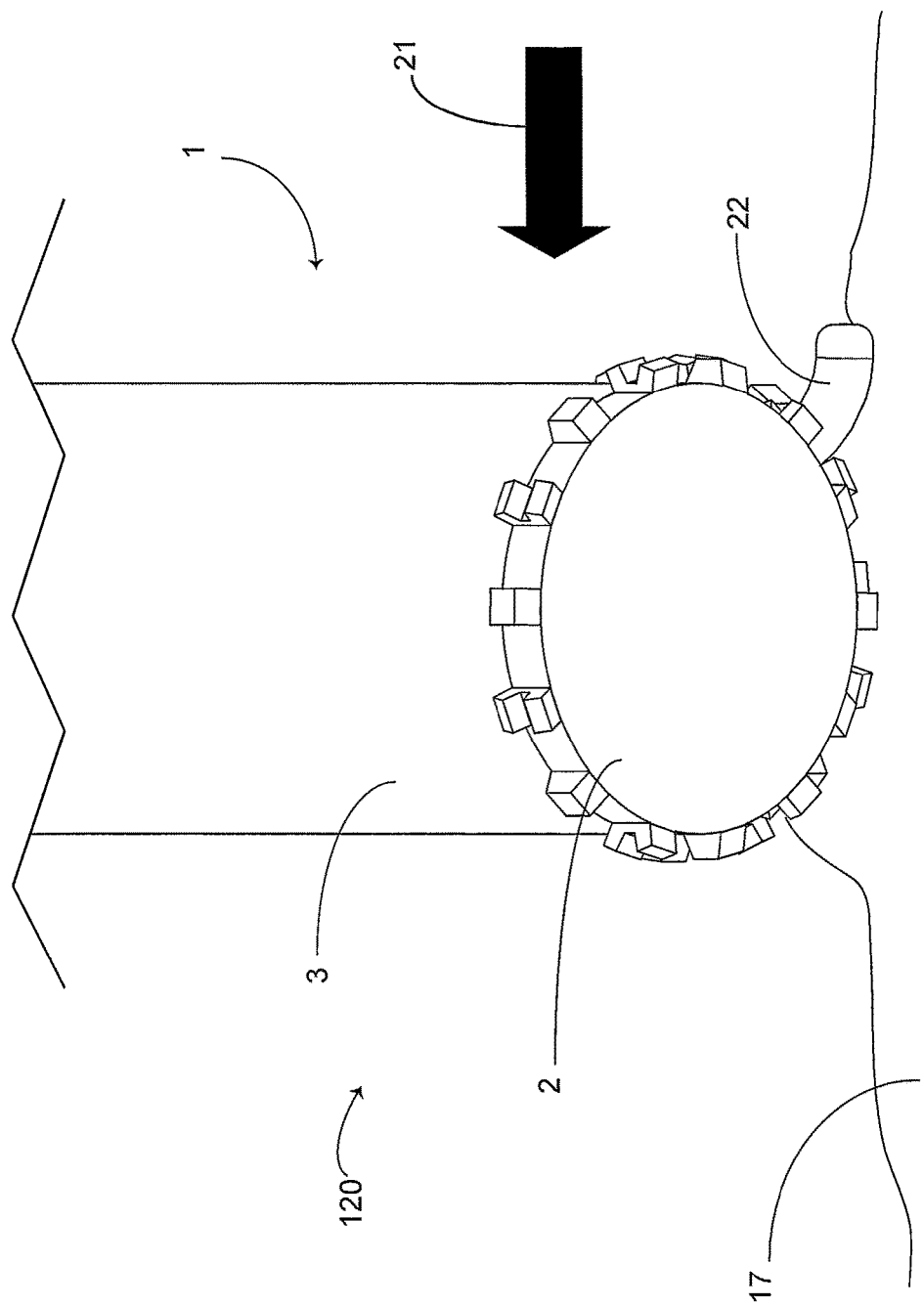

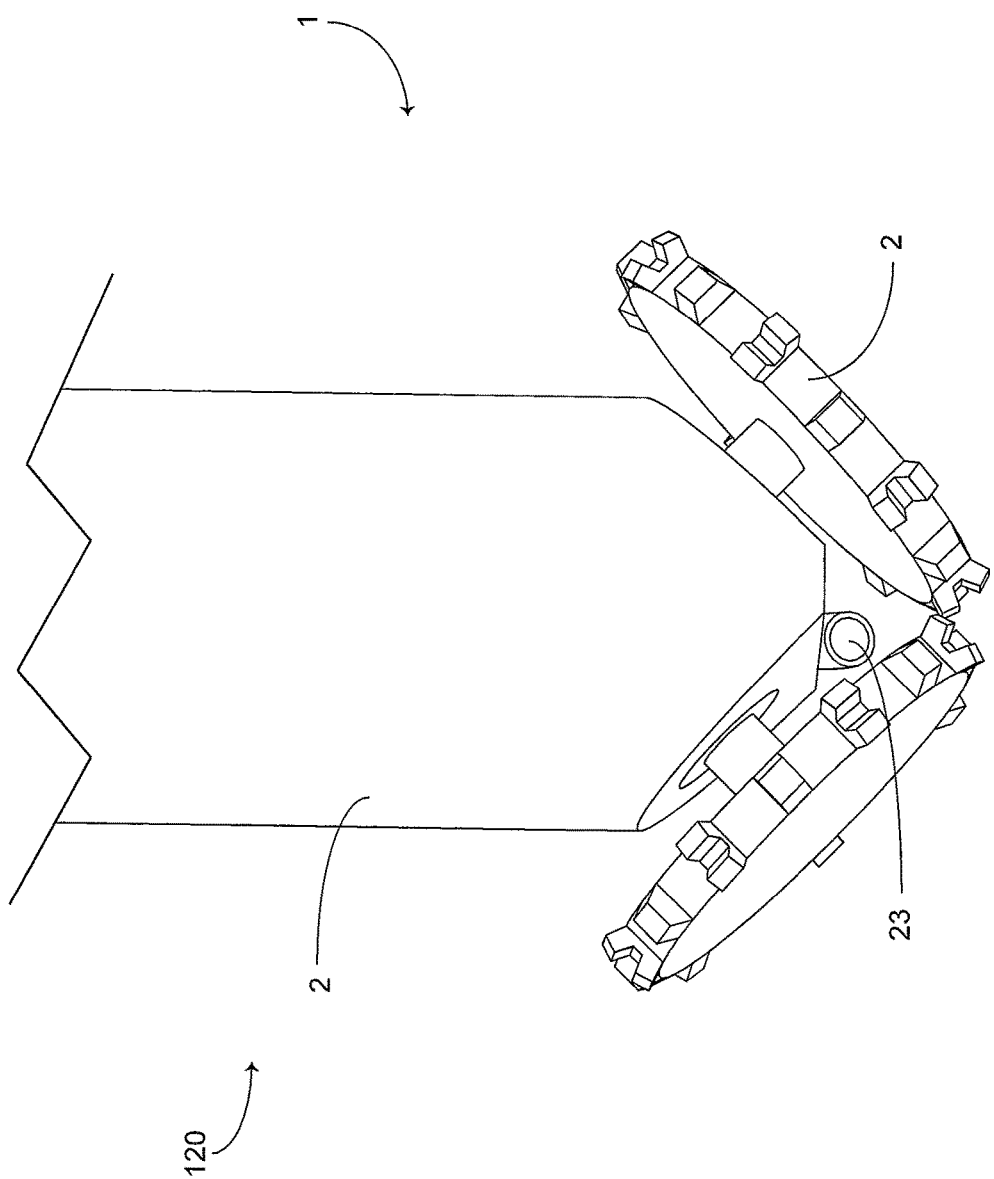

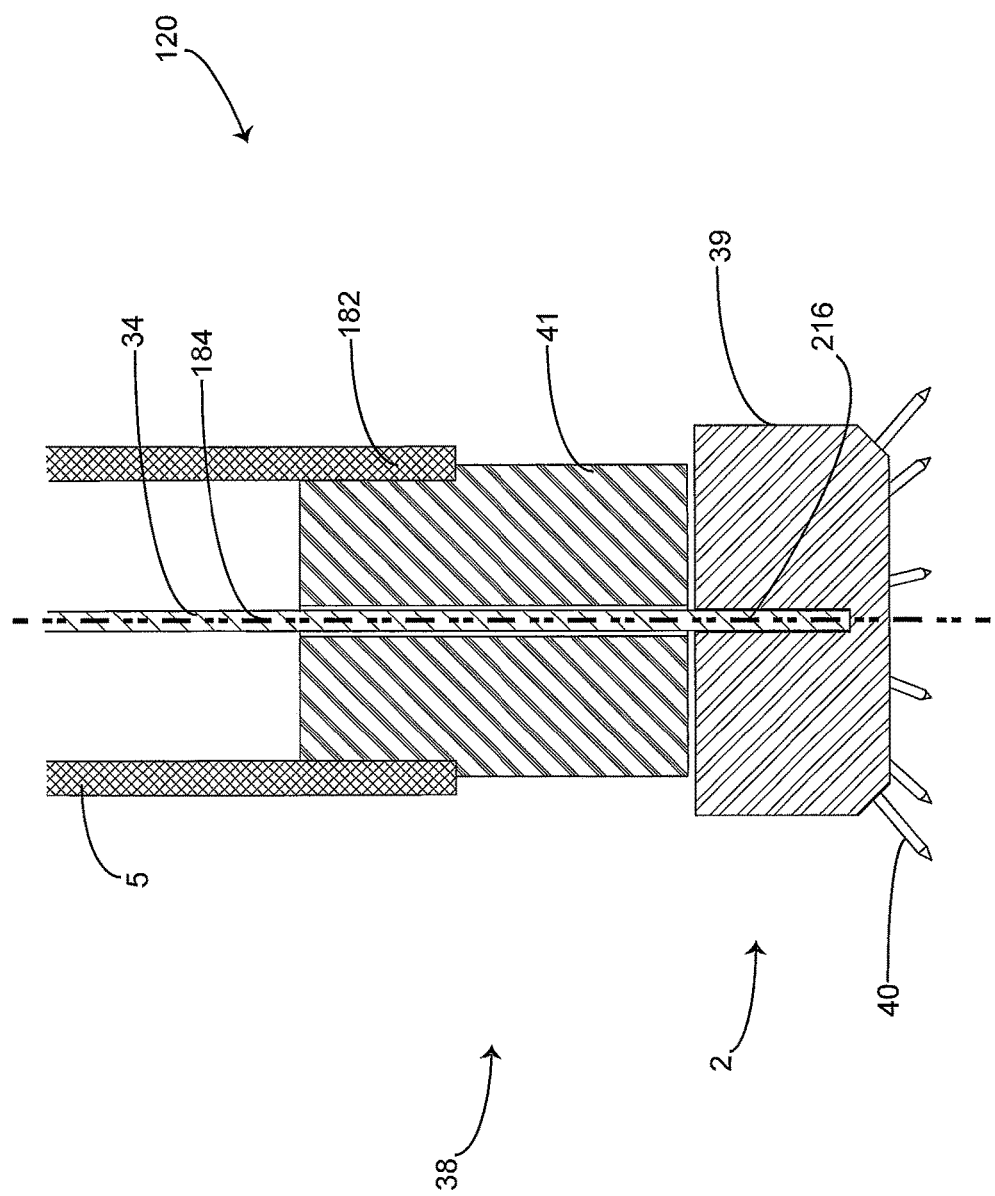

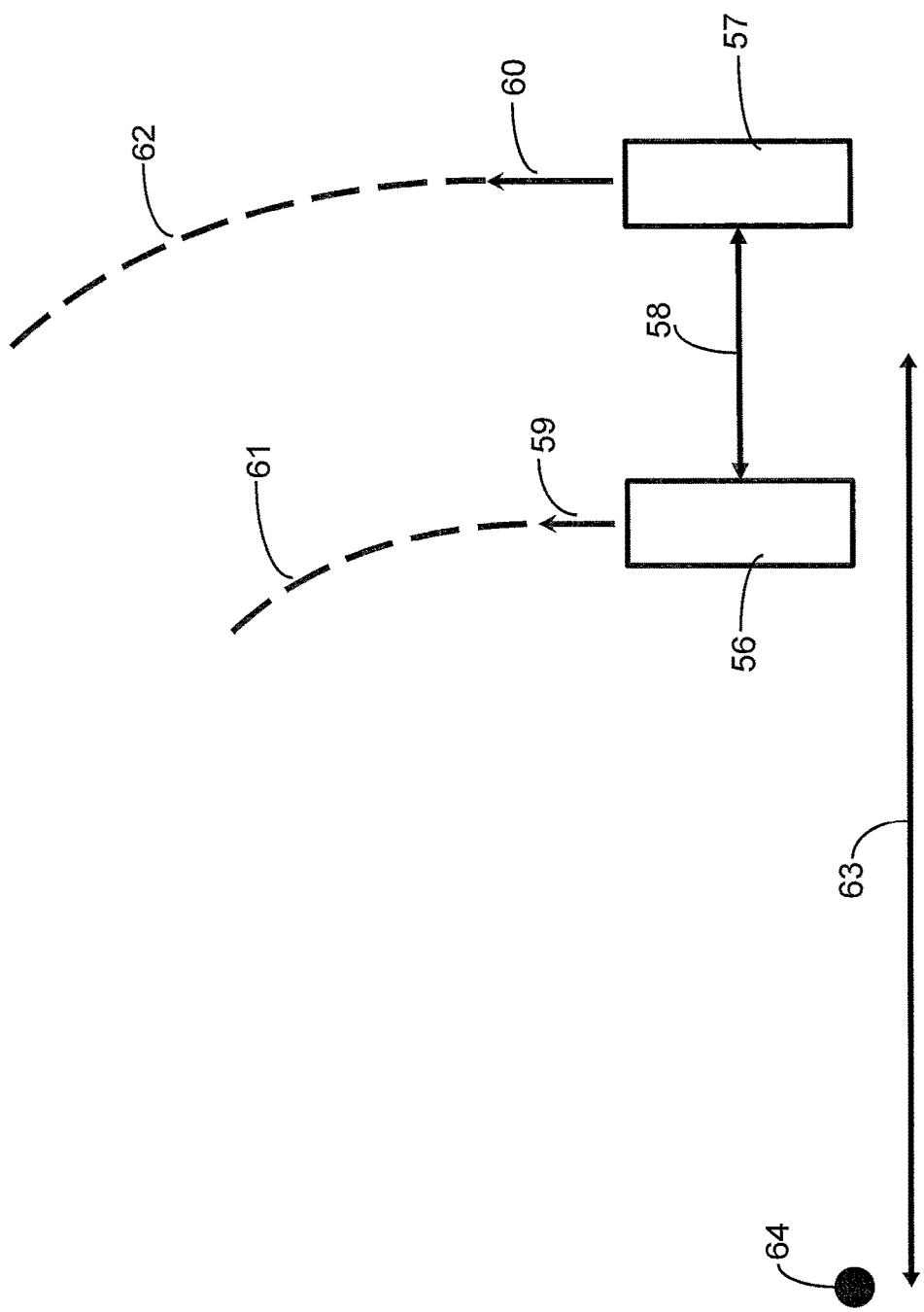

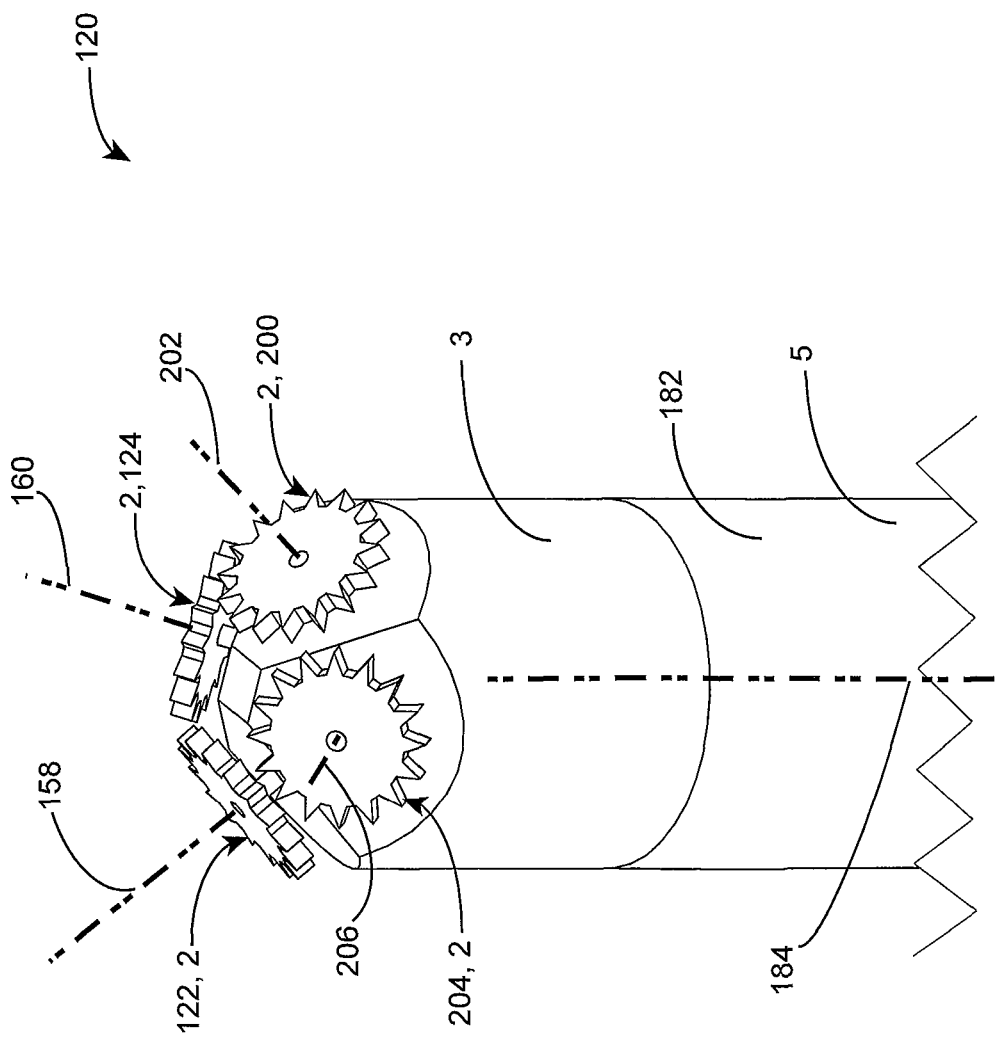

MINIATURE DEVICE PLATFORM FOR NAVIGATION ON MOVING ORGANS

CROSS REFERENCE TO RELATED APPLICATIONS

This patent application claims priority to U.S. Patent Application Ser. No. 61/811,956, filed Apr. 15, 2013 entitled Miniature Device Platform for Minimally Invasive Procedures Inside Active Organs and claims priority to U.S. Patent Application Ser. No. 61/937,912, filed Feb. 10, 2014 entitled Miniature Device Platform for Minimally Invasive Procedures in the Body all of whose entire disclosures are incorporated by reference herein in their entireties for all purposes.

STATEMENT REGARDING FEDERALLY SPONSORED RESEARCH OR DEVELOPMENT

This invention was produced in using funds from the Federal government under National Science Foundation award ID No. IIP-1248522. Accordingly, the government has certain rights in the invention.

BACKGROUND OF THE INVENTION

1. Field of the Invention

The present invention pertains generally to the field of medical devices and more specifically to a system to an improved system for delivering therapy.

2. Background

Atrial fibrillation (AF) affects 2-3 million Americans, costing the healthcare system an estimated $6.65 billion per year to treat. When a patient has AF, the normal depolarizing wave that produces near synchronous activation of cardiac cells in the atrial chambers of the heart is disrupted and coordinated activity ceases. When this occurs, the blood pools in the atrial chambers and does not eject effectively into the ventricles, leading to fatigue, dizziness, nausea, increased risk of clot formation and stroke, and ultimately heart failure.

Normally, the depolarization wave that produces atrial contraction is initiated by pacemaker cells in the sinoatrial (SA) node in the right atrium. In patients suffering from AF, groups of cardiac cells outside the SA node become hyperactive and produce secondary depolarization wave fronts that interact with the normal depolarization wave front, leading to chaotic timing of cardiac cell contractions. Initially, the AF episodes may be few and far between, with the heart able to recover on its own (Paroxysmal AF), but left untreated, the episodes become more frequent and ultimately transition toward Persistent AF, a condition much more difficult to treat. The AF triggering foci responsible for producing atrial fibrillation are located in the pulmonary veins (PV) in the vast majority of cases.

One of the most common procedures for preventing future AF events from occurring is radiofrequency (RF) catheter ablation or cardiac ablation. The goal of cardiac ablation is to electrically ablate and/or isolate AF triggering foci from the rest of the heart to prevent an AF occurrence. Cardiac ablation can be performed epicardially through open heart surgery, via small chest incisions, or endocardially via a catheter-based approach. Catheter-based ablation is the least invasive and is therefore preferable to minimize recovery times and infection rates. In catheter-based ablation, a catheter is fed through a blood vessel in the groin up into the heart and across the septum into the left atrium. The catheter has a metallic tip that is used to deliver high frequency electrical current to tissue. The current locally heats up (ablates) the tissue and as the ablation catheter tip is moved across the tissue it creates a variety of lesion patterns that performs a conduction block to isolate AF trigger foci from the remaining healthy heart tissue. Inconsistent and unstable placements of the ablation catheter tip during the procedure can result in lesion patterns that are disjointed and/or of insufficient ablation depth to be effective. In patients with Paroxysmal AF, catheter ablation to isolate the pulmonary veins is 60-80% successful in eliminating AF. Patients with long-term, persistent AF have poorer and more variable outcomes from a single ablation procedure (30-50% success rates). In this cohort, significant remodeling of the atria has occurred and more extensive and complicated ablation patterns may be required to isolate all of the AF sources. Thus, it is estimated a single catheter ablation procedure is successful in long-term elimination of AF in only 30-80% of patients.

Minimally-invasive procedures require deployment of surgical tools and effectors through small incisions in the body and/or in conjunction with other medical instruments. One example of a system for delivery therapy is found in U.S. Pat. No. 8,100,900 to Prinz et al., the contents of which are incorporated by reference herein in their entirety for all purposes.

Referring to prior art FIG. 1, Prinz et al. describes a system for delivering therapy in which a set of gears 2 contained within an end effector 1 rotate inwardly, in opposite directions, in order to grip a section of tissue and provide continuous motion. Once the tissue is gripped, therapy is applied to it. In the case of AF cardiac ablation, the therapy consists of radiofrequency electrical current used to selectively ablate the cardiac tissue, conducted through an electrode 4. All components of the end effector 1 are situated within a housing 3, attached at the distal end of a catheter 5. At the proximal end of the catheter 5, the operator controls the device. This patent application illustrates several novel embodiments to further advance these procedures.

Many procedures utilize flexible steerable catheters to access the treatment areas. With existing catheter-based devices, it is cumbersome to manipulate the distal tip to create adjacent or contiguous lesions or perform other local treatment. The challenge is exacerbated when the target organ tissue is also contracting and/or moving due to respiration, cardiac function, peristalsis or other bodily movement. Other procedures utilize medical instruments (e.g., endoscopes) with small working channels and/or size constraints because of organ size. Holding position during procedures with these medical instruments is extremely difficult due to patient movement, respiration, peristalsis, and other bodily movements. Clinicians often spend several minutes searching for their lost target—reducing the accuracy and effectiveness of treatment. Thus, what is needed is a device capable of gripping tissue, then holding the tissue in position, without negatively impacting the procedure or tissue.

BRIEF DESCRIPTION OF SEVERAL VIEWS OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 4A shows a slider block with nested slide paths based on a mathematical equation.

FIG. 4B is a top plan view of the slider block of FIG. 4A.

FIG. 4C is a front view of the slider block of FIG. 4A that shows an X-plane.

FIG. 4D is a front view of the slider block of FIG. 4A that shows a Y-plane.

FIG. 5 shows the mathematical equation for the nested slide paths.

FIG. 6 illustrates a perspective view of the tooth profile geometry and an overlapping of the gear teeth to aid in grip strength on the slider embodiment.

FIG. 7B is a front view that shows monopolar RF electrical energy being applied through both gears and central electrode.

FIG. 8 is a side view of the implementation of a flexible electrode configuration.

FIG. 9 is a front view that illustrates the integration of a suction tube at the distal portion of the end effector to aid in grip and retention of tissue.

FIG. 14 is a cross-sectional view that illustrates an embodiment utilizing a rotating head with miniature/micro needles in order to grip the tissue and move in an arc.

FIG. 15 is a schematic view that illustrates the methods for independent speed control of each gear in order to achieve various radii of motion.

FIG. 21 is a perspective view of an embodiment of the device containing a plurality of gears.

Figure 1:
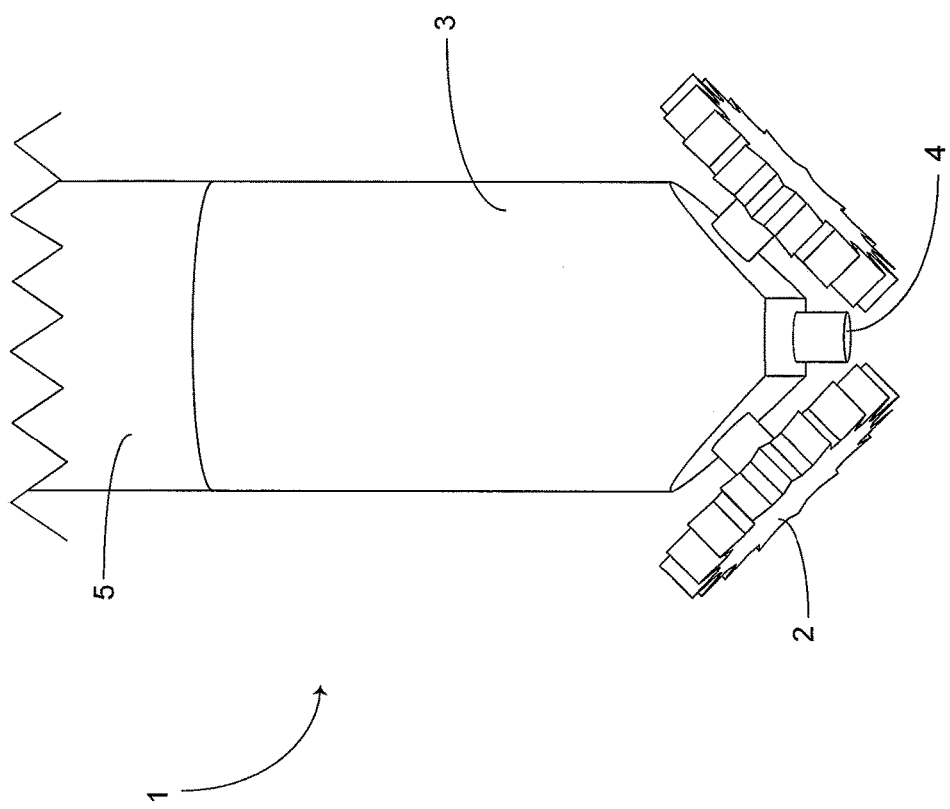
FIG. 1 shows the prior art of the preferred embodiment of U.S. Pat. No. 8,100,900, used for illustrative purposes in this application.
Figure 2:
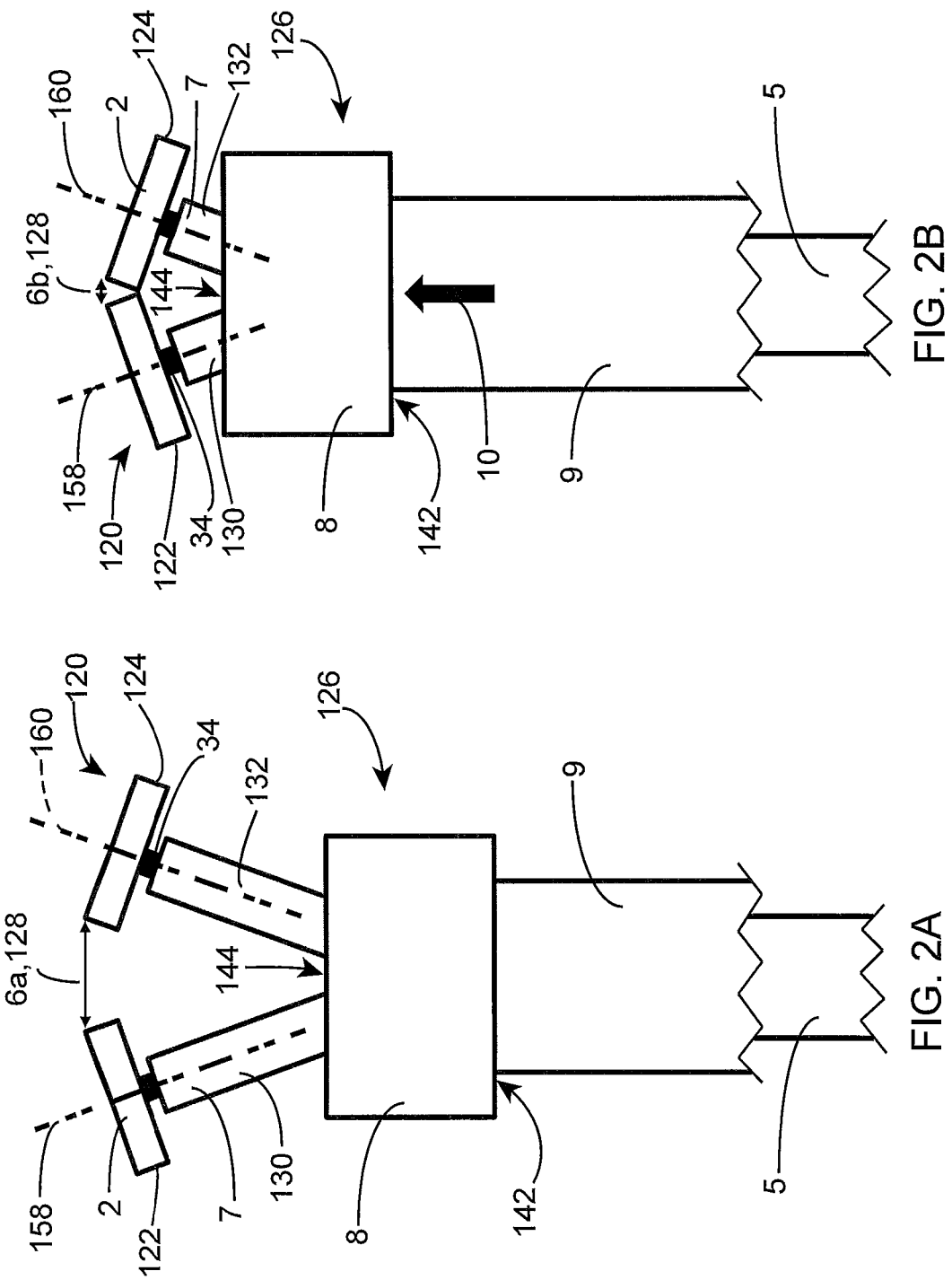
FIG. 2A is a front view that illustrates the basic operation of a sliding housing that facilitates control over gripping and releasing of tissue in which the gears are in an open orientation.
FIG. 2B is a front view of the device of FIG. 2A in which the gears are in the closed orientation.
Figure 3:
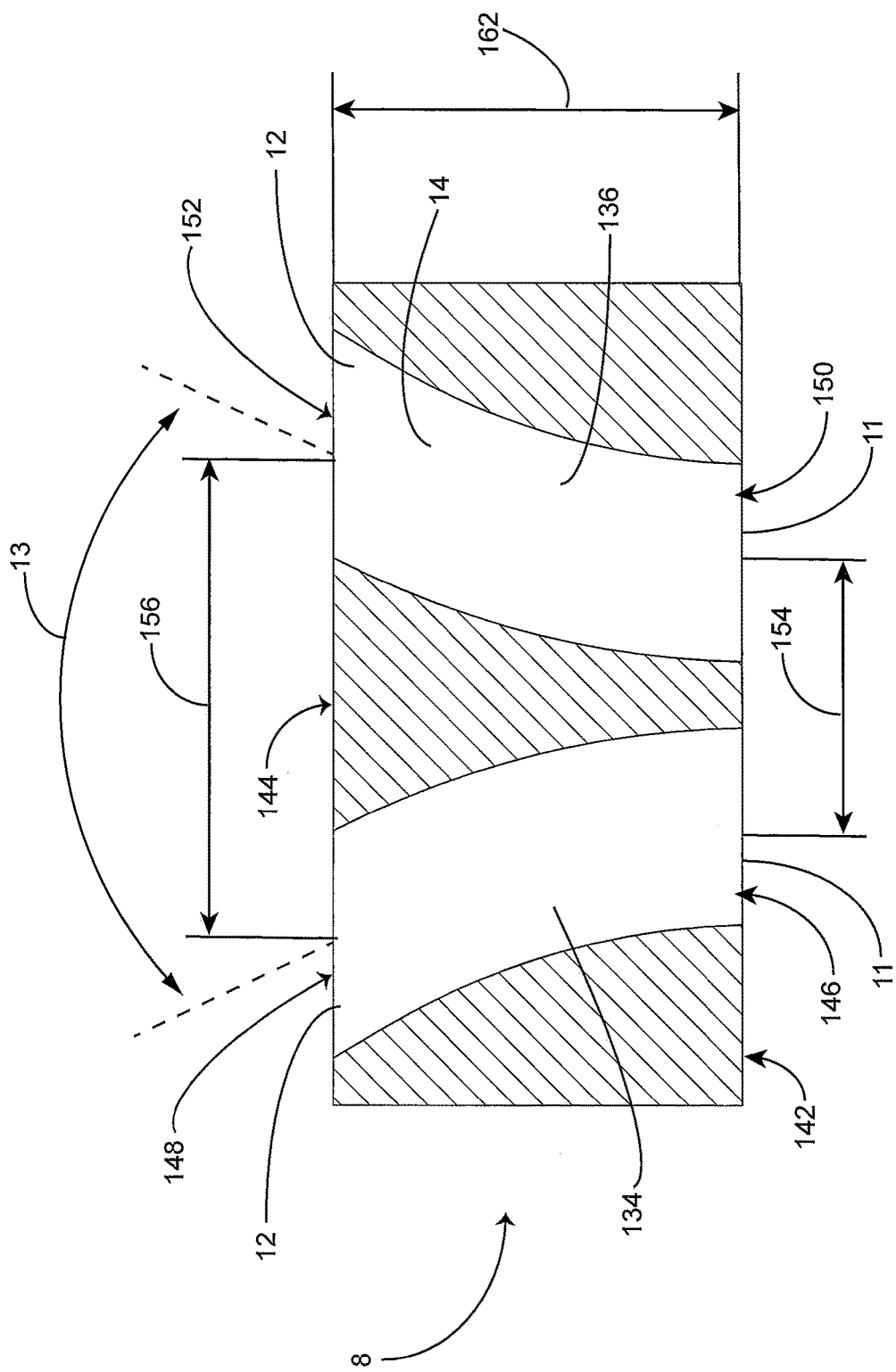
FIG. 3 is a cross-sectional view that illustrates the basic geometry of the slide block.

Repeat use of reference characters in the present specification and drawings is intended to represent the same or analogous features or elements of the invention.

DETAILED DESCRIPTION OF
REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

FIG. 2A through 6 illustrate various methods to enable the operator at-will control (whether through manual or automated means) over gripping and releasing the tissue. A slide block 8, located at the distal end of the device 120 in place of the housing 3. The slide block 8 is situated to the proximal direction of the gears 2, and is able to move axially. The slide block contains two or more lumens 134, 136 through which the slide tubes 7 of the gears 2 pass. In the illustrated embodiments, there are two slide tubes 7 that are designated as the first slide tube 130 and the second slide tube 132. Each lumen 134, 136 contains a path entrance 11 and path exit 12. The slide tubes 7 contain the torque transmission member 34 which connects to the gears 2. The torque transmission member 34 is preferably, but not limited to, a hollow helical stranded wire or tube designed specifically for efficient transmission of torque. Slide tubes 7 are disposed f1 at an exit angle 13, measured at the path exits 12, as to allow the gears to separate or come together as the slide block 8 is moved axially in a sliding motion 10. With the slide block 8 retracted, the open distance 6a between the gears 2 is greatest, to enable the operator to capture a large area of tissue. When the slide block 8 is moved axially in a sliding motion 10, the gears 2 move towards each other to a closed distance 6b, which is much smaller than the open distance 6a. The change in distance applies a force to the area of tissue captured, gripping it securely.

The gears 2 may be further identified as a first gear 122 and a second gear 124. The first gear 122 of the device 120 rotates about a first gear axis of rotation 158, and the second gear 124 rotates about a second gear axis of rotation 160. The axes of rotation 158 and 160 are not parallel to one another and are not perpendicular to one another in the embodiment illustrated. A spacing 128 is present between the two gears 122, 124 such that they do not touch one another. The spacing 128 is controllable due to the adjustability of the positioning of the gears 122, 124. In some arrangements, the gears 122, 124 may touch thus removing the spacing 128.

A spacing mechanism 126 may be present in order to adjust the spacing 128 between the two gears 2. The spacing mechanism 126 may include the slide block 8 that may be connected to an outer sliding catheter 9, concentric to an inner catheter 5, which connects to the operator interface (e.g. handset 42 or console 89) at the proximal end of the device 120, enabling operator control over the sliding motion 10. The outer catheter 9 and the inner catheter 5 may be coaxial with one another. Additionally, a locking mechanism may be placed either at the distal or proximal end of the sliding apparatus, enabling the operator to lock the outer sliding catheter 9 to the inner catheter 5, fixing the spacing 128 between the gears 2 while an operation is performed.

A challenge with the basic slide block 8 design is maintaining a large enough exit angle 13 to facilitate reach and gripping of tissue 17 while keeping the components compact and slide path 14 transitions smooth enough to prevent binding or kinking. With specific reference to FIG. 3, the slide lumens 14 are designated as a first slide lumen 134 and a second slide lumen 136. The first slide lumen 134 receives the first slide tube 130, and the second slide lumen 136 receives the second slide tube 132 such that the second slide tube 132 moves through the second slide lumen 136. The slide block 8 has a proximal end 142 and an oppositely disposed distal end 144. As used herein, the term "proximal" refers to a direction towards the health care provider, and the term "distal" refers to a direction facing away from the health care provider and generally towards the patient or farther inside of the patient. The first slide lumen 134 has a first slide lumen entrance 146 at the proximal end 142, and extends through the slide block 8 terminating at a first slide lumen exit 148 located at the distal end 144. In a similar manner, the second slide lumen 136 has a second slide lumen entrance 150 at the proximal end 142, and a second slide lumen exit 152 at the distal end 144. The slide lumen entrances 146, 148 may be separated from one another by a distance 154 that may be measured from the center of the first slide lumen entrance 146 to the center of the second slide lumen entrance 150. The slide lumen exits 148, 152 can be separated from one another by a distance 156 that may be from the center to center of the slide lumen exits 148, 152. Distance 154 may be less than the distance 156 in some arrangements. Having both slide lumens 14 positioned along a single plane as in FIG. 3 may not be the most efficient use of space and therefore limits the space to make smooth transitions and adequate exit angles 13.

FIGS. 4A, 4B, 4C and 4D illustrate a nested path slide block 36 utilizing nested slide lumens 37 which are based on a mathematical equation given in FIG. 5. The height 162 of the slide block 8 extends from the proximal end 142 to the distal end 144. Since each nested slide lumen 37 is located in its own plane, larger exit angles 13 can be maintained without increasing the overall size of the slide block 8. Each nested slide lumen 37 begins with a lumen entrance 11, and follows the equation shown in FIG. 5 to reach a lumen exit 12. The equation of the center of the nested slide lumens 37 with height are calculated using the overall dimensions and required lumen entrance 11 locations and exit angles 13 for reducing kinking as initial conditions. The nested slide lumens 37 are both mirror images of each other in the X and Y planes. The lumens 134, 136 in extending in the distal direction from the proximal end 142 may be described as first converging towards one another and then diverging from one another.

FIG. 6 illustrates an embodiment for optimizing grip strength utilizing a slide block 8 based design. The gears 2 in this embodiment have teeth 109, 113 designed with a spacing 112 which permits meshing of alternate teeth 110 when the gears 2 are pulled together by sliding the slide block 8 relative to the slide tubes 7. In this regard, the teeth 109 of the first gear 122 enters spacing 112 between alternate teeth 110 of the second gear 124 when the two gears 122, 124 mesh. The meshing of alternate teeth 110 produces a very strong hold on the tissue 17 between the gears 2. The profile geometry of tooth 113 shown but not limited to enhances traction and tissue 17 retention. The tooth 113 may have a cavity therein. The various teeth may be arranged so that teeth 113 are alternatingly disposed about the gears 2. Although not limited to, this embodiment may have benefit in various MIS applications, where a position must be held for an extended period of time while a procedure is performed.

Figure 7A:
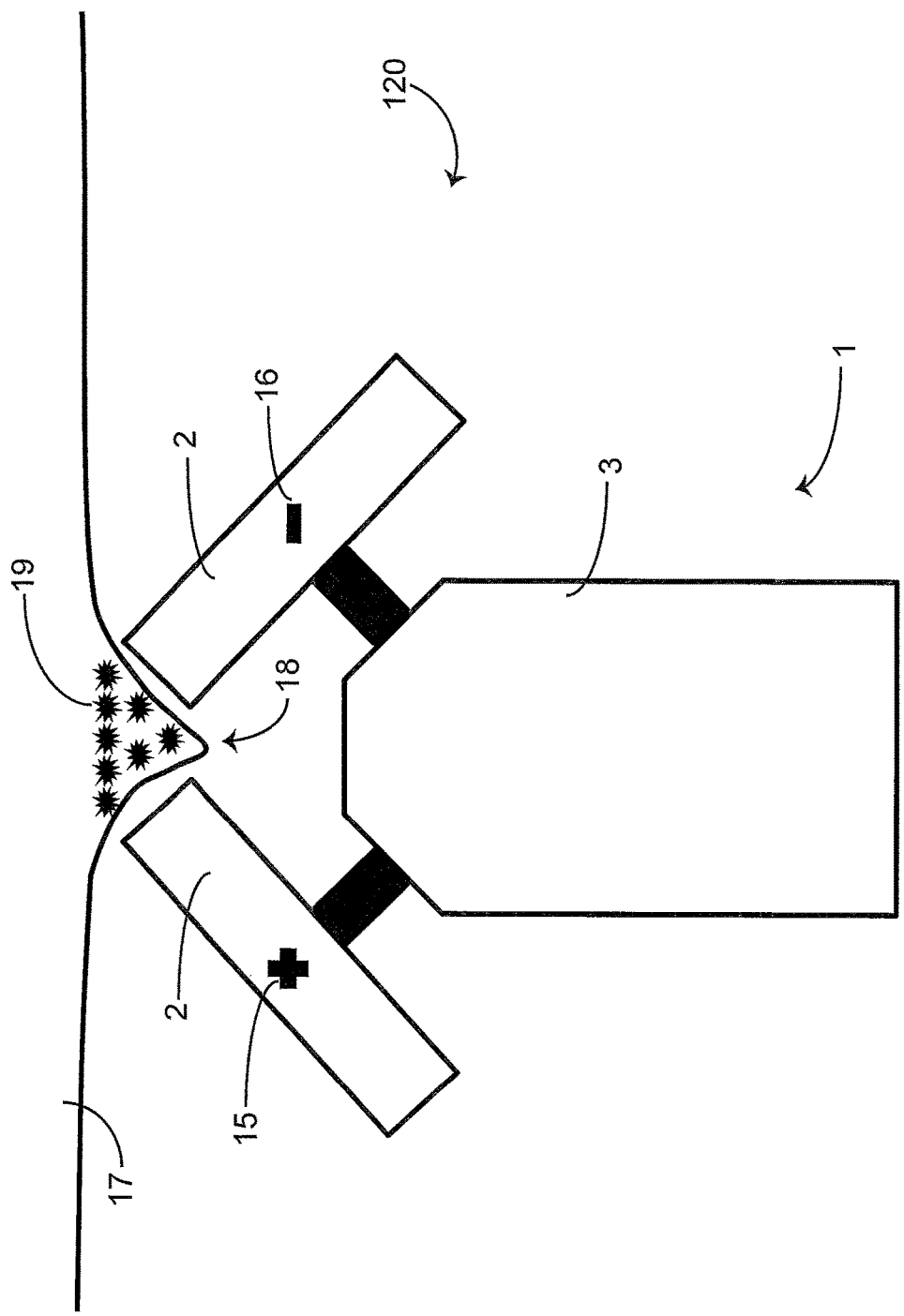
FIG. 7A is a front view that shows bipolar RF electrical energy being applied through the rotating gears.

FIG. 7A illustrates a novel approach for bipolar ablation. With a single monopolar or bipolar electrode 4 as shown in FIG. 1, contact with the tissue 17 over varying conditions (i.e. tissue density, tissue tension, movement, pressure) is not guaranteed, due to its fixed and embedded location. In order to solve this problem, it may be desirable to conduct the RF electrical energy through the gears 2 themselves, guaranteeing that the grasped tissue 18 between them is ablated. This embodiment consists of one of the gears 2 having a positive charge 15, and the other gear 2 being attached to ground 16. The RF electricity will travel from one of the gears 2, through the grasped tissue 18, and out through the other gear 2, creating an area of ablated tissue 19 between the gears 2. The end effector 1 is not limited to the configuration illustrated, but may contain any configuration listed in this application and its prior art.

Furthermore, FIG. 7B illustrates an approach to a monopolar energy being applied. In this case, both gears 2 will carry a positive charge 15. To maximize surface area and coverage, a positively charged 15 central electrode 20 will be located between the gears 2. In the monopolar setup, the patient will have a ground electrode of significantly large area attached elsewhere. The RF electricity will travel highly focused from the gears 2 and central electrode 20 into the grasped tissue 18, creating an area of ablated tissue 19 adjacent to them. The energy will then be dispersed as it travels to the large ground electrode elsewhere on the patient. The end effector 1 is not limited to the configuration illustrated, but may contain any configuration listed in this application and its prior art.

It is possible that it may not be safe or effective to allow electrical energy to pass through the gears 2 in certain applications. In these cases, it may be possible to use an end effector 1 shown as in FIG. 8, in which a flexible electrode 22 makes contact with the tissue 17. Preferably, but not limited to, the flexible electrode 22 would exit the housing 3 in the space between the gears 2, and would be of appropriate length to contact the tissue 17 consistently while the end effector 1 is driving in the direction of forward motion 21 across the tissue 17. The flexible electrode 22 makes contact with the tissue 17, even when the tissue 17 is uneven or its surface varies rapidly. The end effector 1 is not limited to the configuration illustrated, but may contain any configuration listed in this application and its prior art.

In certain therapeutic situations, especially those involving a moving organ, such as a lung or heart, gripping forces created and maintained by the gears 2 alone may not be sufficient. In order to increase the consistency of the grip on the tissue 17, a suction lumen 23 shown in FIG. 9 may be integrated to attract the tissue 17 by application of a negative or vacuum pressure. The suction lumen 23 may be integrated within the catheter 5 of the device 120 or may run outside, adjacent, or parallel to it. At its distal end, the suction lumen 23 may terminate in the space between the gears 2, with a bias in the front, center or rear, relative to the direction of motion of the end effector 1 relative to the tissue 17.

Figure 10:
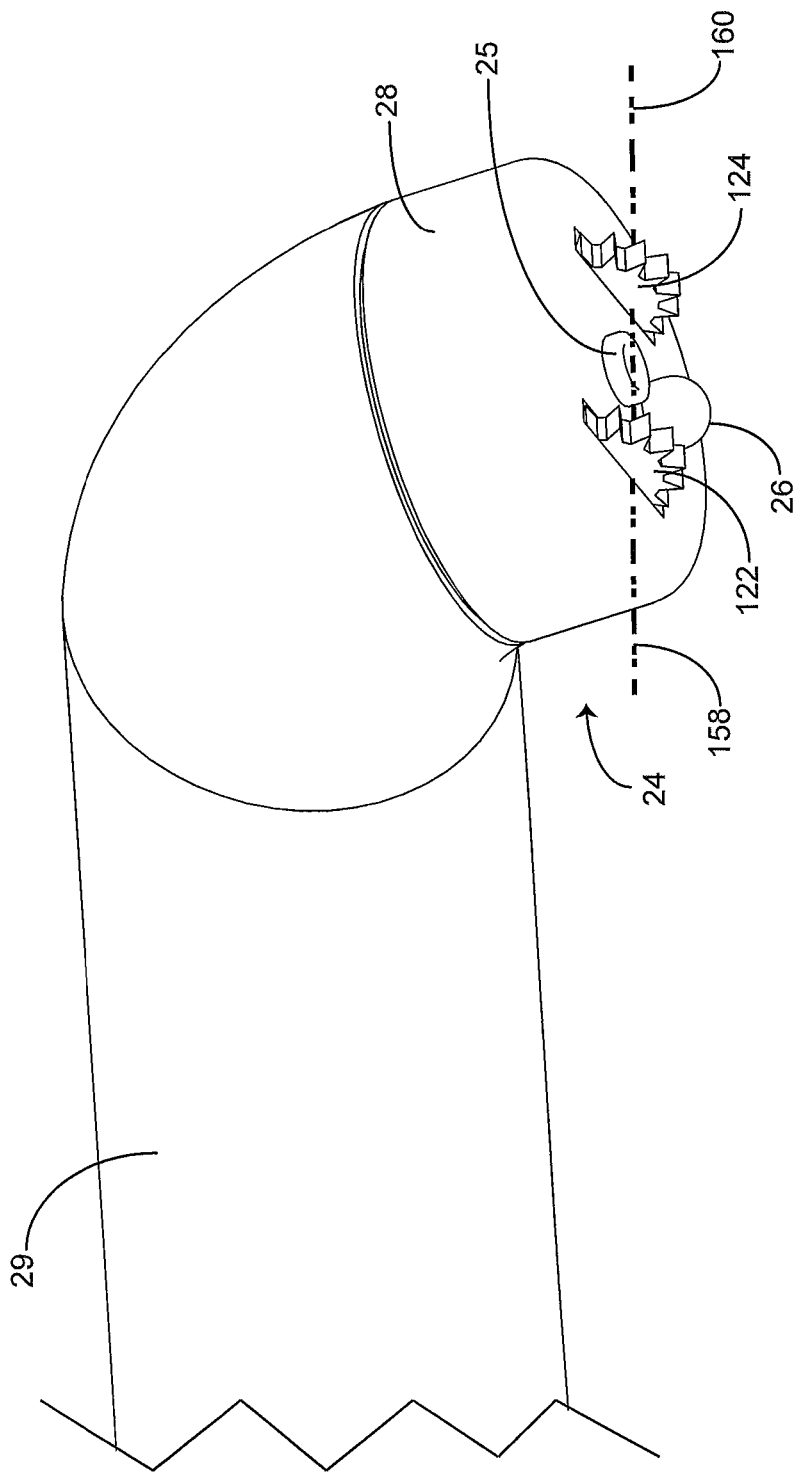
FIG. 10 is a perspective view that illustrates a variation of a suction-based catheter system.

As an alternate embodiment containing suction, FIG. 10 illustrates a suction-based end effector 24 containing two drive gears 122, 124 in preferably, but not limited to, a vertical orientation relative to the tissue. The first gear axis of rotation 158 may be coaxial with the second gear axis of rotation 160. Between the gears 122 and 124, but not limited to the geometric center is a suction port 25, which facilitates grasping of the tissue 17. Adjacent to the suction port 25 is an electrode 26, through which RF electrical energy is transmitted. The electrode may be monopolar or bipolar in design. The pair of drive gears 122, 124 enables operator control over forward and backward motion, as well as motion in an arc or a circle, with a theoretically unlimited range of turning radii. The drive gears 122, 124 can be driven independently from one another such that one drive gear 122 can rotate while the other drive gear 124 is not rotated, or can be driven such that one drive gear 122 rotates in one direction while the other drive gear 124 rotates in an opposite direction.

Figure 12:
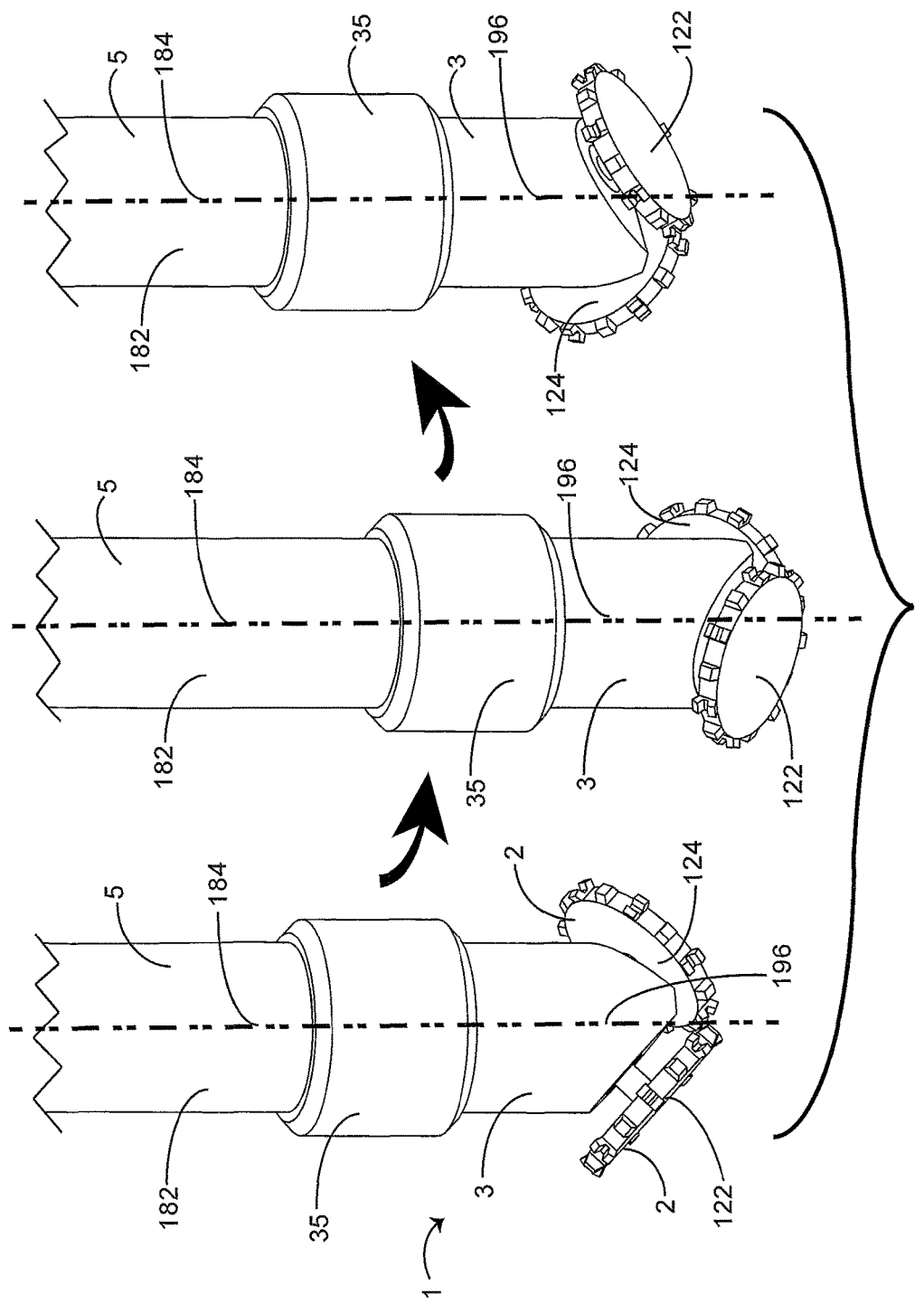
FIG. 12 is a series of three perspective views that show a concept of a rotating head which reduces the torsional stress on the catheter while navigating in a circular or arcing pattern.

In order for an end effector 1 to navigate in an arc or circular motion, it must overcome the torsional resistance of the catheter 5 in order to remain attached to the tissue 17 and complete the motion. FIG. 12 illustrates an end effector 1 coupled to a rotation mechanism 35 located between the end effector 1 and the catheter 5. The end effector 1 is not limited to the configuration illustrated, but may contain any configuration listed in this application and its prior art. The rotation mechanism 35 allows the end effector 1 to rotate independently of the catheter 5 about their longitudinal axes, and contains a mechanism which retains the function of the components contained within the end effector 1. One such mechanism could be composed of a planetary gear system with a centralized gear, unaffected by the rotation of the end effector 1 which couples to the driving gears 2. Another example of a rotation mechanism 35 could be a low-resistance bushing or bearing.

The rotation mechanism 35 has a rotation mechanism axis of rotation 196 that may be coaxial with a catheter distal end longitudinal axis 184 of a distal end 182 of the catheter 5. The rotation mechanism 35 can cause the gears 122, 124 to rotate about the axis of rotation 196 such that the gears 122, 124 rotate completely 360 degrees relative to the axis 184 of the distal end 182. This rotation about axis 196 is independent of the rotation of the gears 122, 124 about their own axes 158, 160. However, in some arrangements, the device 120 can be configured such that rotation about axis 196 likewise causes the gears 122, 124 to be driven such that they are also, simultaneously driven around their respective axes 158, 160.

Figure 13:
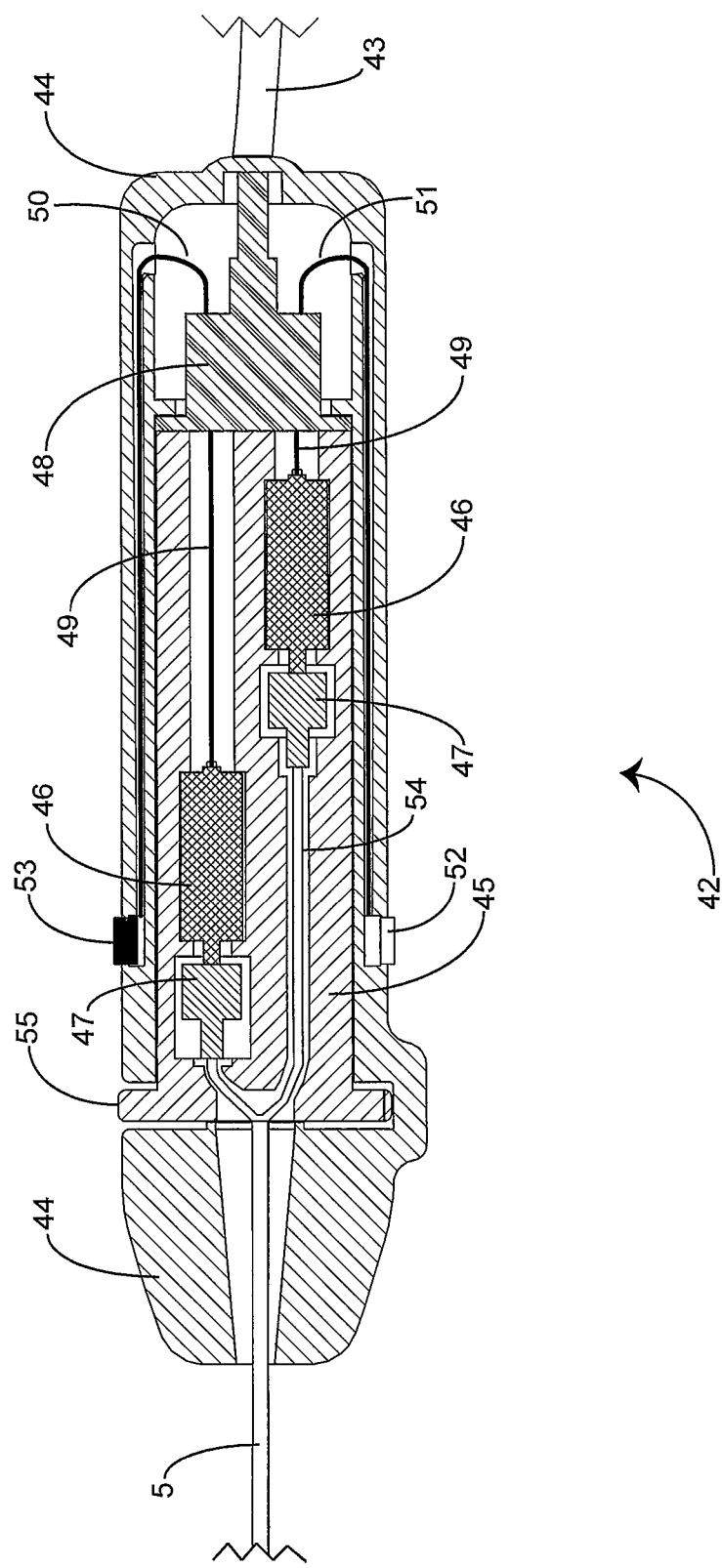
FIG. 13 is a cross-sectional view that illustrates a handset located on the proximal end of the device featuring an embodiment which enables rotation of the catheter and end effector to aid steering.
Figure 22:
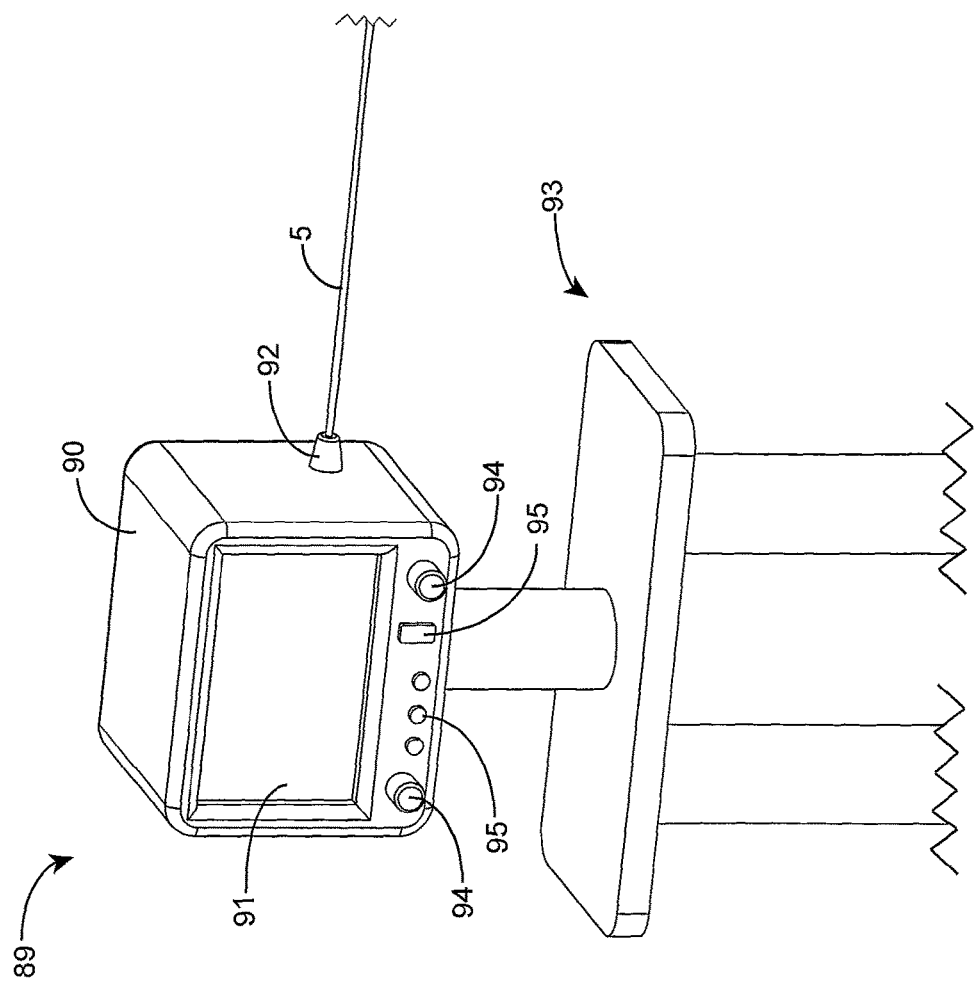
FIG. 22 is a perspective view of a console located on the proximal end of the device in which the user interfaces.

FIGS. 13 and 22 illustrate user interfaces for the control of the device 120. These embodiments in FIGS. 13 and 22 may be coupled with any of the end effector embodiments contained in this application, and vice versa.

FIG. 13 shows a full catheter system containing a handset 42 which enables rotation of the catheter 5 and drive system independent of the handset 42. Enabling this motion assists the clinician in repositioning and redirecting of the end effector 1 along the tissue 17. The end effector 1 is not limited to the configuration illustrated, but may contain any configuration listed in this application and its prior art. Additionally, an end effector 1 driving in an arcing motion will apply a torsional stress to the catheter 5, which will overcome the end effector 1 grip force on the tissue 17, releasing its hold. A system which allows rotation will release the torsional stress. In this embodiment, a catheter 5, with one or more torque transmission members 34 extends through a sheath 54 into an inner handset 45. The inner handset 45 is located centrally to and surrounded by the outer handset 44, which contains function controls, including but not limited to drive system, ablation, suction, and irrigation, on its exterior surface. A control means 55 (knob or lever) is rigidly connected to or is part of the inner handset 45 and protrudes from the front, rear or sides of the outer handset 44. The operator uses the control means to rotate the inner handset 45, catheter 5, and end effector 1 or its components independently of the outer handset 44. Located between the inner handset 45 and outer handset 44 is a slip ring 48, enabling the electrical connections from the controls located on the outer handset 44 to be connected with the rotating inner handset 45 without tangling or additional torsional stress placed on those electrical connections. Additionally, a similar mechanical device may be located to allow irrigation or suction to pass through the interface without kinking or breakage. Within the inner handset 45 are one or more drive motors 46 or drive mechanisms attached to the torque transmission member 34 through a mechanical coupler 47. Each drive motor 46 connects through a torque transmission member 34 to a single gear 2, although alternately a single drive motor 46 could be routed through a single torque transmission member 34 to two or more gears 2. In such a setup, however, a coupling mechanism at the distal end, near the gears 2, may be necessary to transmit the motion from only a single torque transmission member 34. The drive motors 46 are connected via motor power wires 49 to a slip ring 48 located within the inner handset 45. At the proximal end of the slip ring, a drive switch wire 51, whose purpose is to give the operator control over the drive motor 46, is routed through an outer handset 44 to a drive switch 52. An ablation switch 53 is located on the outer handset 44 with an ablation switch wire 50 routed through the outer handset 44 and to the slip ring 48, which is then routed through the inner handset 45 and catheter 5, giving the operator control over the ablation function. Any additional electrical functions are also routed through the slip ring 48 in the manner described above. The power sources for all electrical functions exit the distal end of the slip ring 48 and are contained in a power wire bundle 43, which connects to the individual or integrated power supplies for each function.

FIG. 22 illustrates a console 89 for control of the device in the embodiments contained herein. A console 89 may be desirable in order to free up the hands of the operator to complete other tasks during the procedure. The console 89 contains a console housing 90 which includes a display screen 91, control knobs 94, control buttons 95, and any necessary internal electrical or mechanical componentry. The display screen 91 may be, but not limited to, a standard LCD or LED display, or may be a touchscreen display, used in lieu of some or all of the control knobs 94 and control buttons 95. The control knobs 94 and control buttons 95 may control functions such as, but not limited to: irrigation, ablation, aspiration, grip control/strength, individual gear drivelines, and deflection of the catheter tip. A catheter connection 92 facilitates attachment of the catheter 5 and its integral functions.

FIG. 14 illustrates a simplistic rotating head end effector 38 concept in which a rotating head 39 equipped with a gripping member 40, which could be constructed of but not limited to, miniature or micro needles, is attached to a torque transmission member 34. The torque transmission member 34 is routed through a stationary (non-rotating) housing 41, which is attached to a distal end 182 of the catheter 5. The rotating head 39 is applied to a section of tissue 17. The gripping member 40 will maintain traction on the tissue 17 and the rotating motion of the rotating head 39 will force the rotating head end effector 38 to move along the surface of the tissue 17 in an arcing motion due to the rotating head 39 being the only point of contact with the tissue 17. RF electrical energy can be conducted directly through the rotating head 39, providing that the material of its construction is electrically conductive.

The rotating head 39 has a rotating head rotational axis 216 that is coaxial with the catheter distal end longitudinal axis 184. The various needles extending making up the gripping member 40 extend from the rotating head 39 in the distal direction at an angle that is not parallel to and is not perpendicular to the rotating head rotational axis 216. The torque transmission member 34 may be a single torque transmission member 34 such that a second torque transmission member 34 is not carried by the catheter 5.

FIG. 15 illustrates the concept of controlling the inner drive gear 56 and outer drive gear 57, relative to a rotation pivot point 64, in order to control the rotation radius 63 of an end effector 1 on the tissue surface. Knowing the gap 58 between the contact points of the inner drive gear 56 and outer drive gear 57, the ratio of the inner drive gear velocity 59 and outer drive gear velocity 60 can be used to control the rotation radius 63 of the end effector. By having an inner drive gear velocity 59 that is less than the outer drive gear velocity 60, the inner drive path 61 will be shorter than the outer drive path 62 for a given amount of time, forcing the device to turn on a rotation radius 63 about an arbitrary rotation pivot point 64.

Figure 16B:
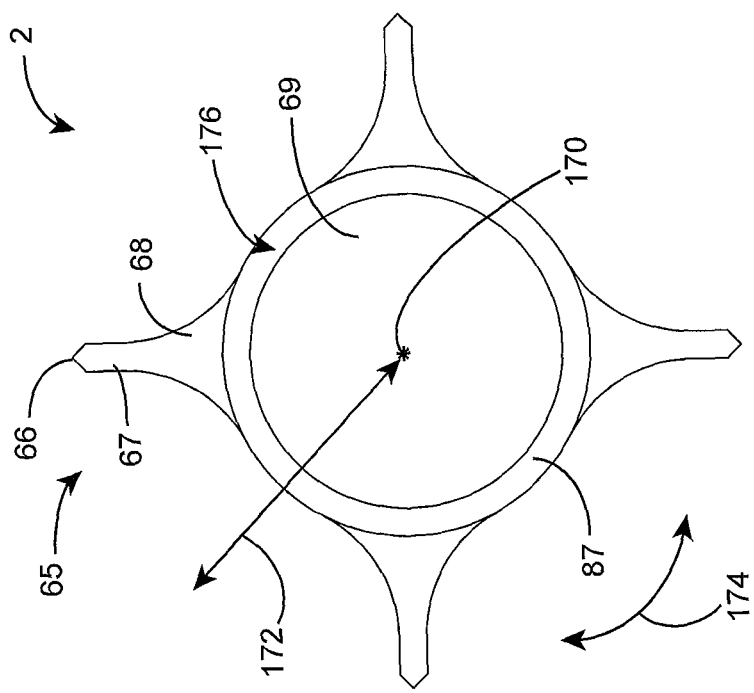
FIG. 16B is a top view of the gear design of FIG. 16A.
Figure 16A:
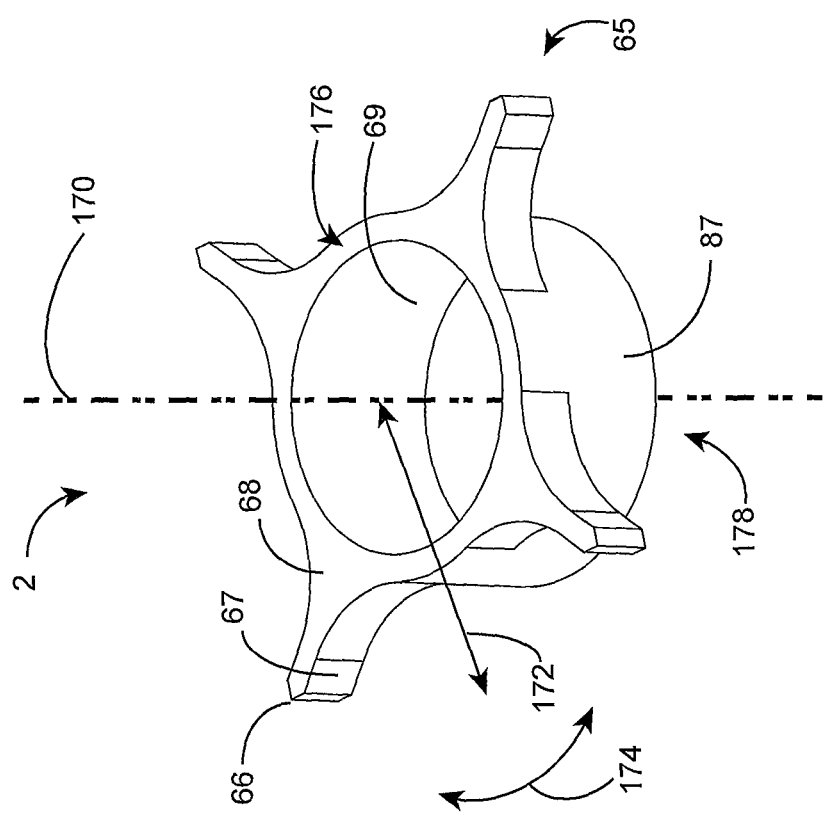
FIG. 16A is a perspective view that illustrates an embodiment of a gear design.

FIGS. 16A and 16B illustrate a gear 2 design concept with gear tooth 65 geometry to enable traction on tissue 17, while limiting depth of penetration into tissue 17—preventing snagging of tissue 17, and preventing tissue damage. At the distal tip of each gear tooth 65 is a penetrating point 66. The penetrating point 66 is fabricated to high accuracy or sharpened in order to penetrate into the tissue 17, providing traction while navigating. Moving away from the distal tip of the gear tooth 65, radially inwards in the radial direction 172 towards the center of the gear 2 having the gear axis of rotation 170 is a thin, small diameter gear tooth shaft 67. The gear tooth shaft 67 permits penetration into the tissue 17 along its length, which is from 0.050 to 1.5 mm but more preferably from 0.100 to 0.500 mm.

The gear tooth shaft 67 widens at its proximal end into a gear tooth base 68. The arc length direction 174 is the direction around the gear axis of rotation 170 that circles the gear axis of rotation 170. The widening may be accomplished such that the arc length direction 174 subtending the width of the gear tooth shaft 67 increases as the radius 172 decreases to the gear base 87 to form gear tooth base 68. The widening may also be arranged such that gear tooth base 68 does not decrease at all in an arc length direction 174 from the gear tooth shaft 67 to the gear base 87. The gear tooth base 68 may thus have the same or greater distance in the arc length direction 174 in the radial direction 172 inwards from the gear tooth shaft 67 to the gear base 87. This widening profile is a penetration depth control feature, and could be, but is not limited to: radial, parabolic, bulb-like, linear, or stepped in geometry. Widening can provide a gradual or immediate resistance to penetration, limiting the depth of penetration of the gear tooth 65 into the target tissue 17. Limiting penetration depth can reduce risk of tissue perforation, prevent snagging of tissue, and/or tissue damage.

Figure 17:
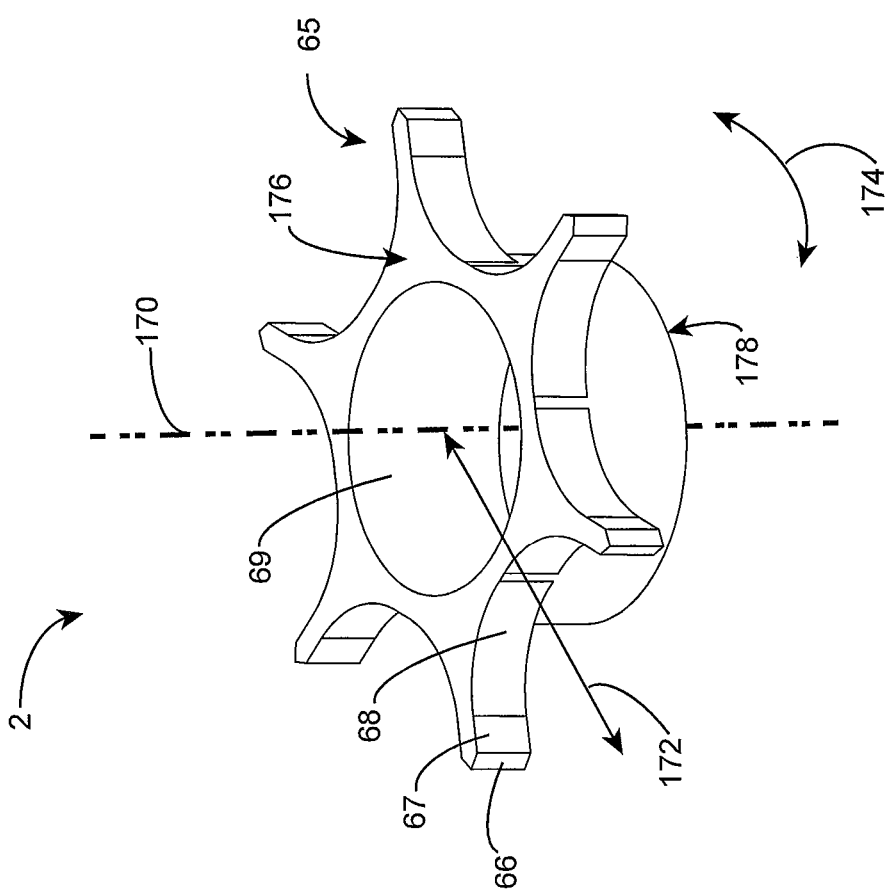
FIG. 17 is a perspective view of an embodiment of a gear design with geometry shown in FIG. 16A showing an increased number of teeth.

FIG. 17 illustrates a similar gear embodiment, having an increased number of gear teeth 65. The number of gear teeth 65 may range from 2 to 12, more preferably from 4 to 8. Within the gear base 87 is a bore 69 to accept a drive member 34, such as but not limited to stranded aircraft wire or a hollow helical wound torque transfer wire.

Figure 18A:
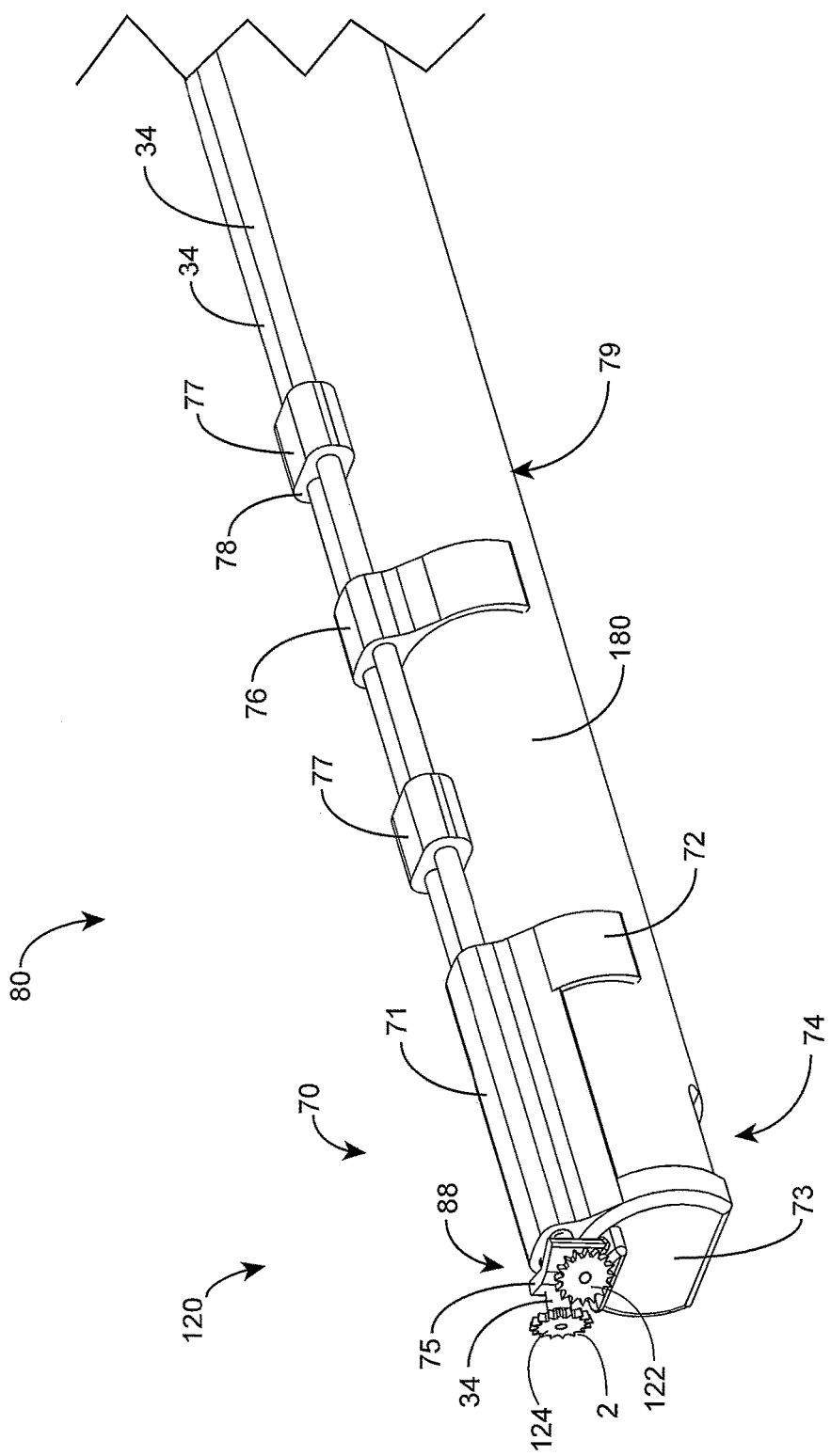
FIG. 18A is a perspective view that illustrates an embodiment of the device mounted to a medical instrument, such as an endoscope.

FIG. 18A illustrates a medical device with a clip-on end effector 80. The clip-on end effector 70 is primarily located at the distal end of the medical instrument to which it is being attached, such as but not limited to an endoscope 79. The clip-on end effector 70 is comprised of a clip-on housing 71. In order to fit securely, a distal end cap 73 is applied over the endoscope 79, and a housing retention clip 72 is secured to the outer surface 180 of the body of the endoscope 79. The clip-on housing 71, distal end cap 73, and housing retention clip 72 are designed such that the functional area 74 of the endoscope 79 is left unobstructed and capable of its intended functions. Gears 2 are located on the distal end of the clip on housing 71 incorporated into a slider-type mechanism 88. The torque transmission member 34 is routed through an angled slider plate 75, causing the distance between the gears 2 to widen as the torque transmission member 34 is moved linearly along the device axis. The torque transmission members 34 pass through the clip-on housing 71 and are routed alongside the endoscope 79. Additional retention clips 76 may be attached at various length intervals to provide stability to the routing. Alignment collars 77 which conduct the torque transmission members 34 through collar bores 78 are placed at various length intervals to prevent the torque transmission members 34 from twisting or tangling with each other.

The angled slider plate 75 may move relative to the outer surface 180 of the endoscope 79 and relative to first and second slide tubes 130, 132 or torque transmission members 34. This sliding action may cause the first and second gears 122 and 124 to move closer to and farther from one another as previously discussed due to the fact that the angled slider plate 75 is arranged to cause the tubes 130, 132 to extend away from one another in the distal direction. Alternatively, the angled slider plate 75 may be fixed stationary relative to the outer surface 180 of the endoscope 79. In this arrangement, the first and second slide lumens 130, 132 or the torque transmission members 34 can move in the distal and proximal directions relative to the outer surface 180 through the angled slider plate 75 to again cause the first and second gears 122, 124 to move closer to and farther from one another.

Figure 18B:
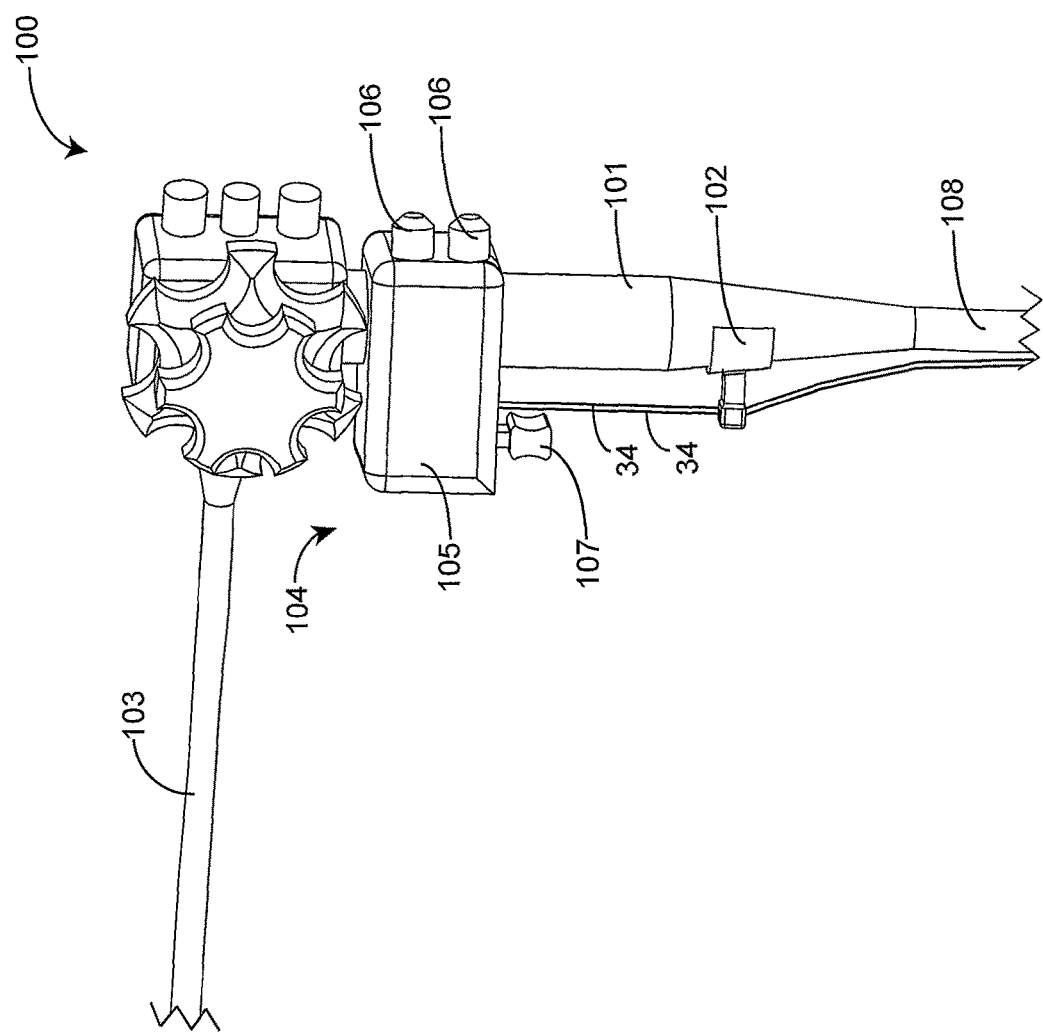
FIG. 18B is a perspective view that illustrates the proximal end of the embodiment shown in FIG. 18A, including controls for the user.

FIG. 18B illustrates a potential control solution for the proximal end of the medical device with clip-on end effector 80. At the proximal end of the insertion tube 108 of an endoscope 79 is an endoscope control body 100 which contains controls for various functions of the endoscope 79, such as lights/illumination, camera, irrigation, gas, suction, and tip manipulation. The endoscope 79 has a lightguide tube 103. To enable a clip-on end effector 70 to be used with the endoscope 79, the operator must have end effector controls 104 to utilize the additional functions the clip-on end effector 70 provides. From the proximal end of the insertion tube 108, the device widens into a control body handle 101, which is held by the operator. The end effector control 104 consists of a control housing 105, which snaps, clips, or fastens otherwise to the control body handle 101. The control housing 105 contains drive equipment and electrical circuitry necessary for the operation of the clip on end effector 70, which is typically a set of gear motors, wiring, and power switch(es). One or more motor control buttons 106 are located within the control housing 105. A grip control lever 107 controls the spacing between the gears 2 and the grip strength by either moving a piece equivalent to the slide block 8 of embodiment shown in FIGS. 2A through 6 or the torque transmission members 34 themselves. The torque transmission members 34 are routed parallel and alongside the insertion tube 108, with a control body retention clip 102 securing them in a desirable position.

Figures 19A, 19B:
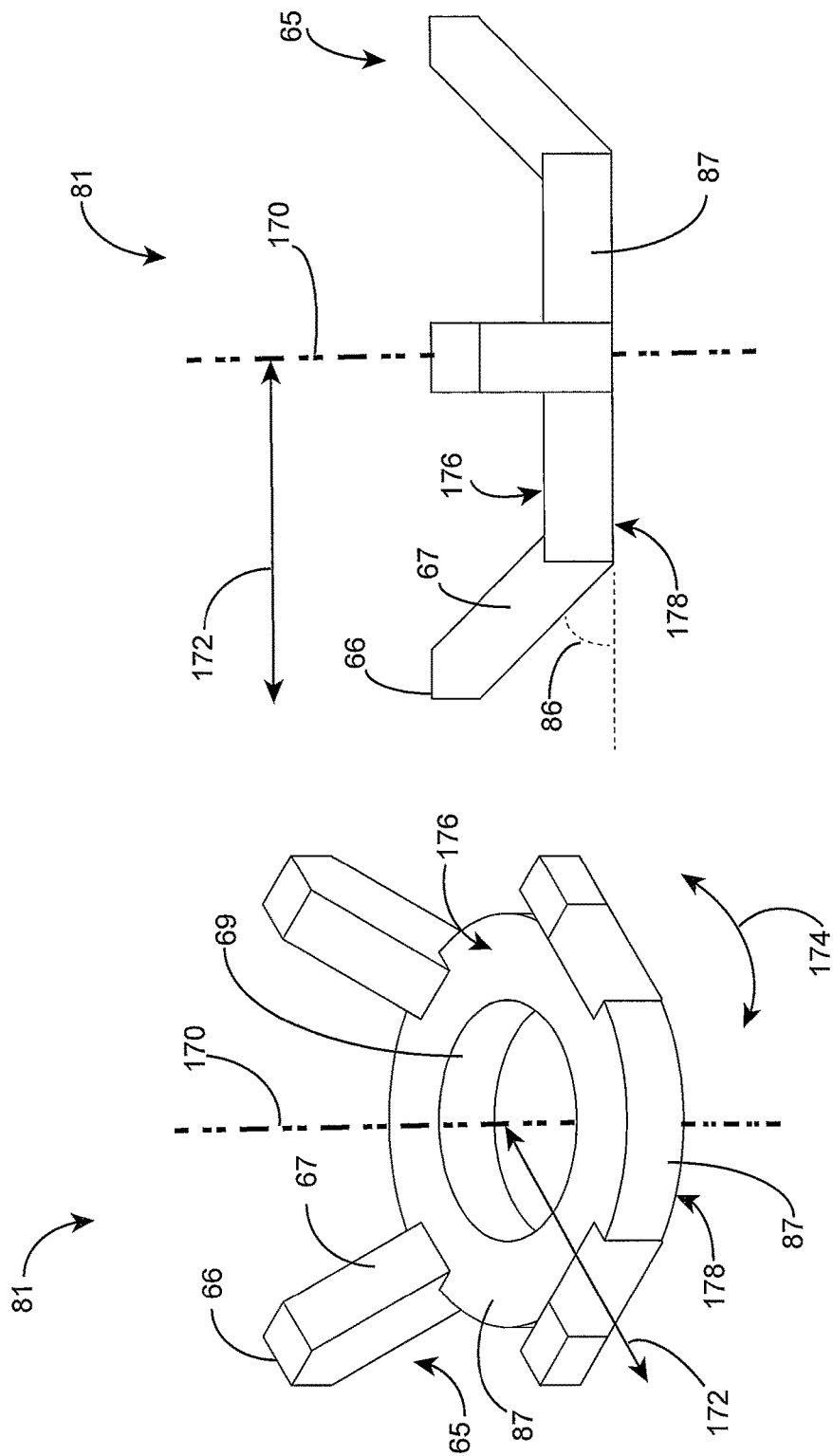
FIG. 19A is a perspective view of a gear design with angled teeth.
FIG. 19B is a side view of the gear design of FIG. 19A.

FIGS. 19A and 19B illustrate an angle tooth gear 81. The angle tooth gear 81 has gear teeth 65, which may range in number from 2 to 12, but more preferably from 4 to 8. In this embodiment, the gear tooth 65 has a gear tooth shaft 67 whose axis is disposed at an angular offset, or tooth angle 86 relative to the gear base 87. Although a gear tooth base 68 is not present, in other embodiments the gear tooth base 68 could be disposed between the gear tooth shaft 67 and the gear base 87. Also, although the gear tooth shaft 67 is shown as having a linear, consistent shape, it may be varied in other embodiments so as to be of a variety of shapes. In the embodiment illustrated, the gear base 87 has an upper surface 176 and an oppositely disposed lower surface 178 that are separated from one another in a direction along the axis of rotation 170. The gear tooth shaft 67 is oriented at a tooth angle 86 to the lower surface 178 that may be from 25-65 degrees. The tooth angle 86 may be constant along the entire length of the gear tooth shaft 67. The gear tooth shaft 67 is oriented at an obtuse angle with respect to the upper surface 176. The tooth angle 86 may be from a line that extends outward in the radial direction 172 from the lower surface 178 to the gear tooth shaft 67.

At the furthest distal end of the gear tooth shaft 67, a penetrating point 66 is present which penetrates a small amount into the target tissue 17 to provide grip and traction. Within the gear base 87 is a bore 69 to accept a torque transmission member 34, such as but not limited to stranded aircraft wire or a hollow helical wound torque transfer wire. The angle tooth gear 81 may be utilized to enable greater grip. Additionally, two (2) could be mounted axially on a torque transmission member 34, but maintain an angle between them which grips tissue well, such as in FIGS. 20A and 20B.

Figure 11:
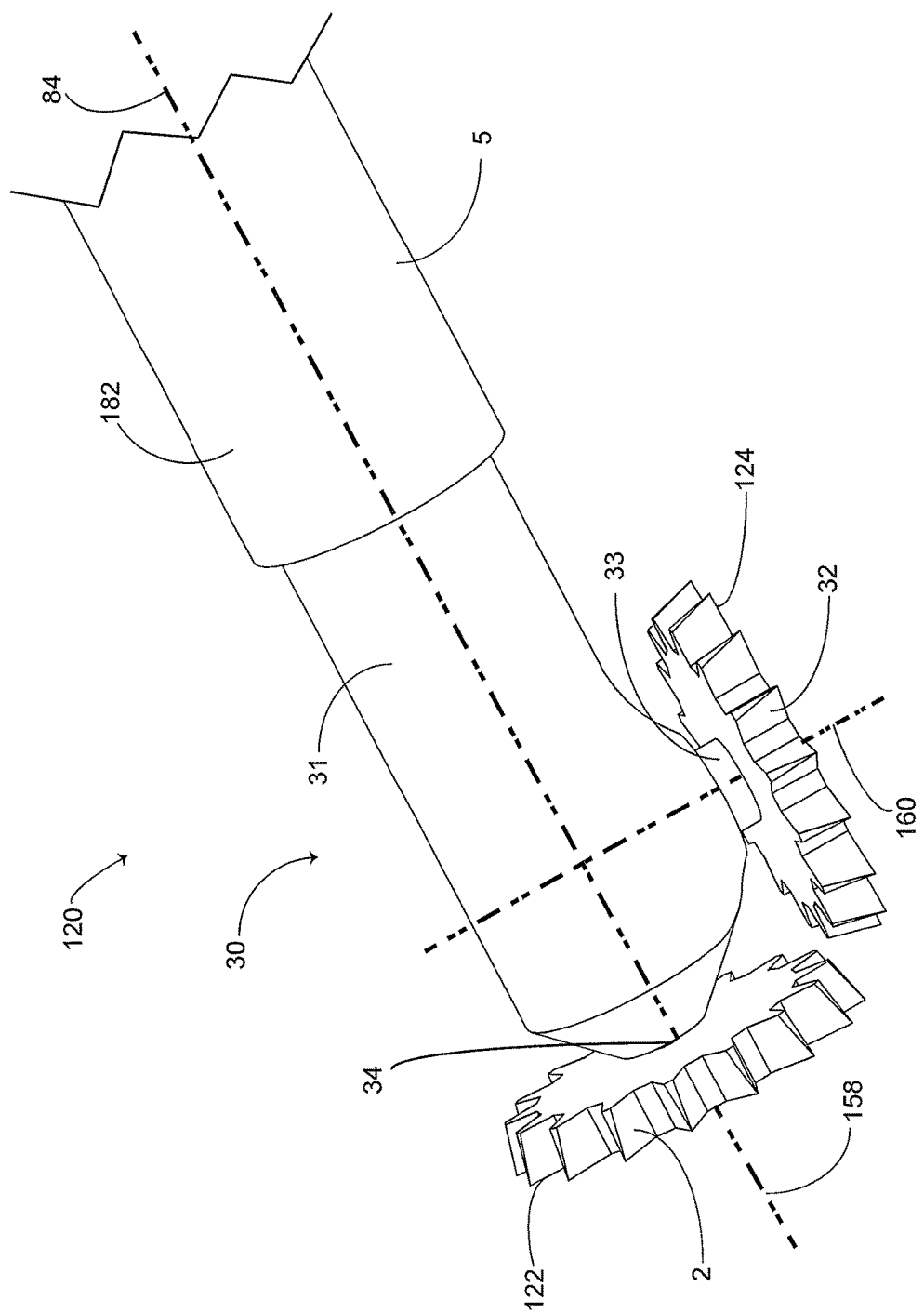
FIG. 11 is a side view that illustrates an alternate embodiment utilizing an asymmetrical end effector to promote tissue navigation in a circular or arcing pattern.
Figure 20A:
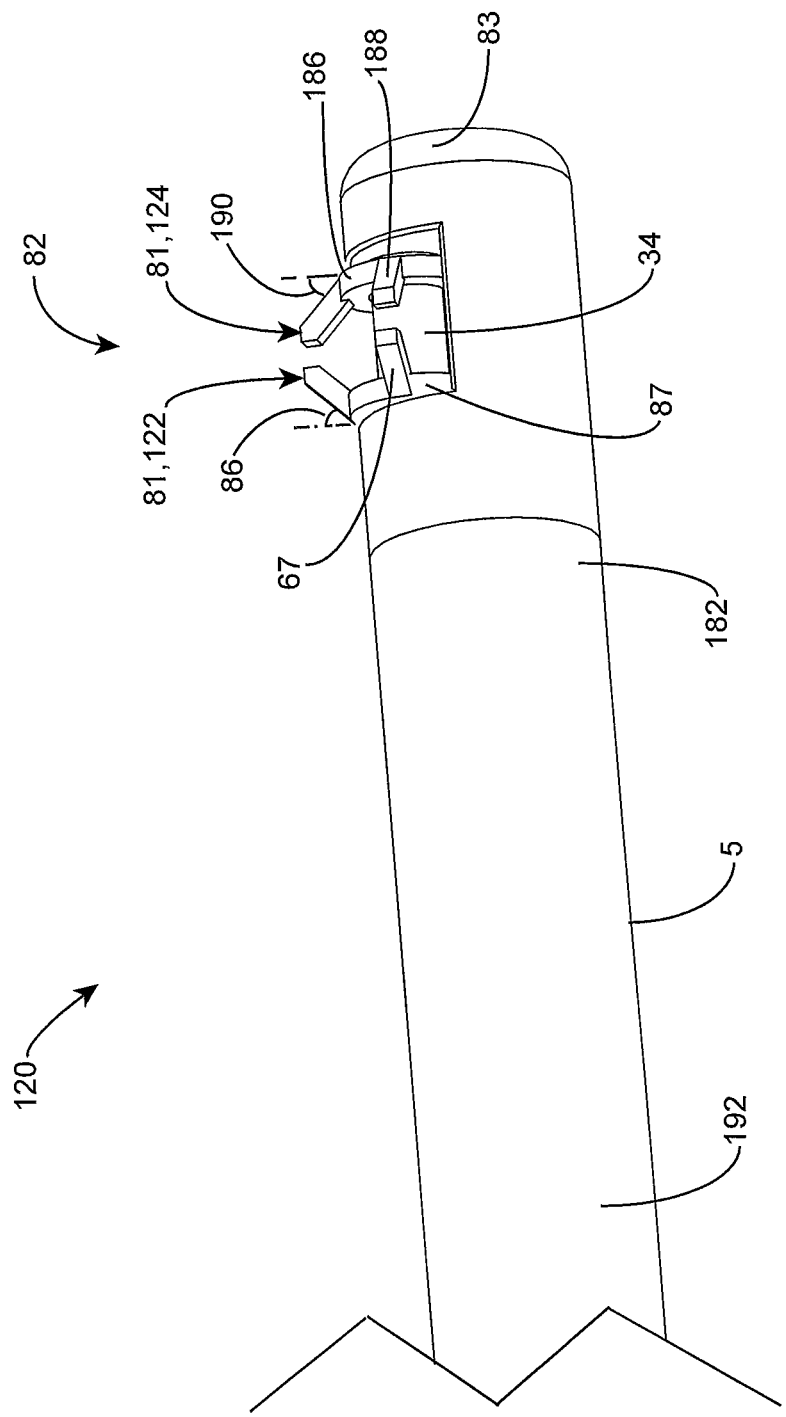
FIG. 20A illustrates a perspective view of an embodiment of the device used in minimally invasive procedures.
Figure 20B:
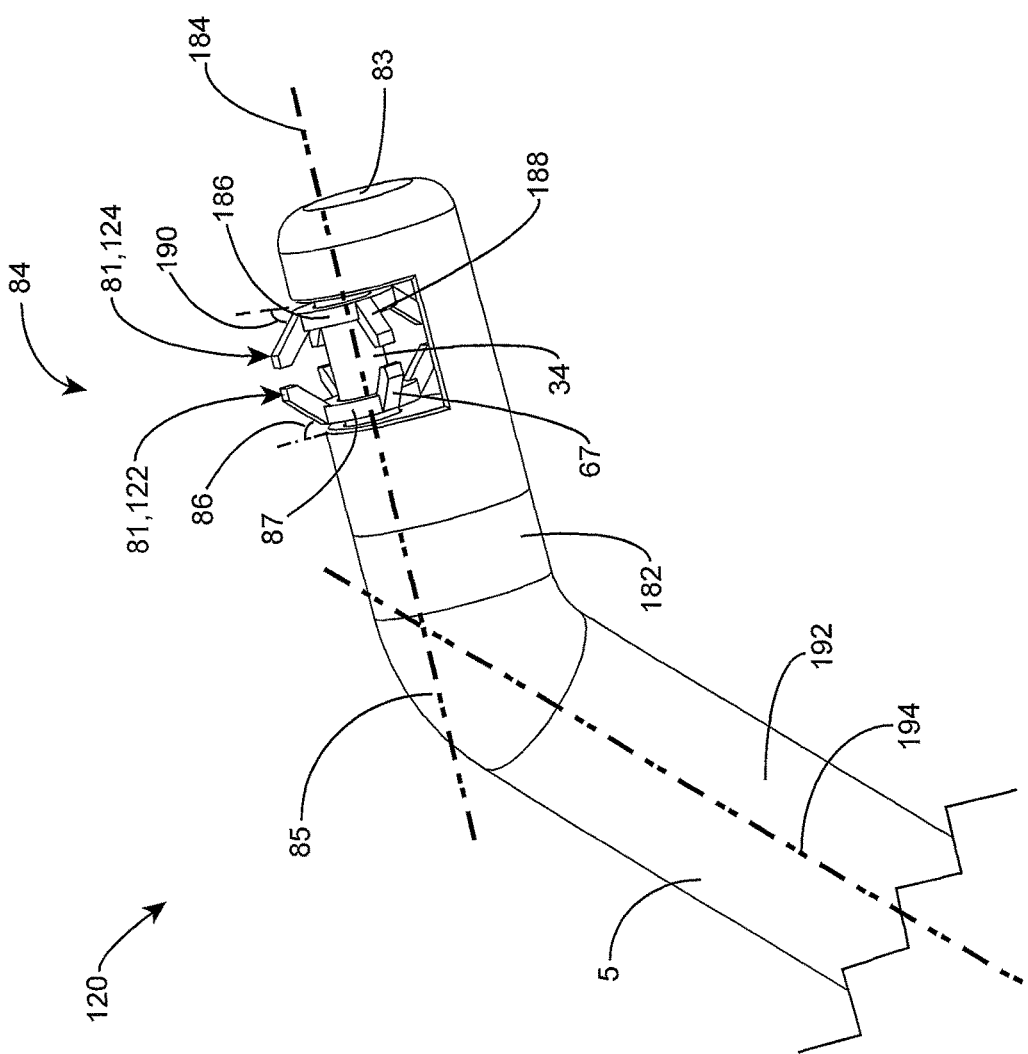
FIG. 20B illustrates a perspective view of an embodiment of the device used in minimally invasive procedures showing a deflection, permanent or temporary, in the catheter tip.

FIGS. 11, 20A and 20B refer to embodiments of a miniature device platform utilizing a single torque transmission member 34. A single torque transmission member 34 may be desired for manufacturing simplicity and/or ability to scale the device to fit into smaller size footprints. The change in the angle of approach that using a single torque transmission member 34 provides may also be advantageous in being able to navigate in an arc or circular motion. The device 120 may be arranged such that only a single torque transmission member 34 is present to provide torque to the gear(s) 2, and such that a second torque transmission member 34 is not present. In this regard, all of the gear(s) 2 of the device 120 are rotated by a single torque transmission member 34 if at all, and none of the gears 2 are rotated by a separate torque transmission member 34. As such, multiple gears 2 may be driven by a single torque transmission member 34 such that none of the gears 2 of that device 120 are driven by a separate torque transmission member 34.

As shown in FIG. 11, an asymmetric end effector 30 is used to achieve a different approach angle, containing an asymmetric housing 31, which allows a driven gear 2, 122 to be rotated and be aligned on the longitudinal axis of the catheter 5. The catheter 5 has a distal end 182, and the distal end 182 has a catheter distal end longitudinal axis 184. The first gear axis of rotation 158 is thus coaxial with the catheter distal end longitudinal axis 184. Eliminating or reducing the angle that a torque transmission member 34 has to overcome will increase the fluidity of motion and efficiency of the system. Tissue 17 is able to be grasped due to pairing with a passive gear 32, 124 that is able to rotate freely via a freewheeling hub 33, whose axis 160 is disposed at an angle perpendicular to the first gear axis of rotation 158 and the catheter distal end longitudinal axis 184.

FIG. 20A illustrates a device 120 with side mounted gears 82 comprising of two angle tooth gears 81 mounted to a single torque transmission member 34. As discussed with reference to the embodiment in FIGS. 19A and 19B, the teeth angle 86 of the angle tooth gears 81, permits the same tissue 17 gripping function of other embodiments using dual drive members in the present invention, with the simplicity of a single drive member. An end cap 83, houses the components and auxiliary functions including but not limited to electrodes 26 (for ablation applications), irrigation outlets, and aspiration inlets 25. The end cap 83 is attached to a catheter body 5 which extends towards the proximal end of the device 120.

The first angle tooth gear 122 is configured so that its gear tooth shaft 67 extends from the gear base 87 in the distal direction. The second angle tooth gear 124 has a second gear base 186 from which the second gear tooth shaft 188 extends. The second gear tooth shaft 188 is arranged at a second gear tooth angle 190 to a line extending from the bottom surface of the second gear base 186 in the radial direction as previously discussed with reference to other exemplary embodiments. The second gear tooth shaft 188 extends from the second gear base 186 in the proximal direction of the catheter 5 and thus towards the first angle tooth gear 122. Actuation of the single drive member 34 causes both of the angle tooth gears 122, 124 to rotate at the same time and at the same amount due to the fact they are driven by the same member 34.

FIG. 20B shows a deflected device with side mounted gears 84, this embodiment is a variation of the embodiment illustrated in FIG. 20A, which additionally includes a deflection 85 between the catheter 5 and end cap 83 to aid positioning of the end effector during the procedure. The deflection 85 may be either permanent or temporary. If temporary, the deflection 85 may be activated by cable action at the proximal end of the catheter 5. The deflection 85 can be arranged so that it is located between the distal end 182 of the catheter 5 and a catheter body 192 of the catheter 5. The angle tooth gears 81 are located at the distal end 182 and are completely distal from the deflection 85. The catheter body 192 has a catheter body longitudinal axis 194. The deflection 85 causes the catheter body longitudinal axis 194 to be angled with respect to the catheter distal end longitudinal axis 184 such that these axes 194 and 184 are not coaxial or parallel with one another.

FIG. 21 illustrates an embodiment containing a plurality of gears 2 mounted on an end effector housing 3. The end effector housing 3 is located distal to a distal end 182 of the catheter 5. In this embodiment, the gears 2 may vary in number from 3 to 8, but more preferably 3-4. Multiple gears 2 can enable larger degrees of freedom (DOF) of the device 120, including but not limited to: linear, up to 3 axis, and rotary. Tissue engagement can potentially benefit as well, having a larger number of areas of engagement where gears 2 are in close proximity. Similar to other embodiments, this embodiment attaches to a catheter 5 towards its distal end 182 and may include other functions, such as irrigation, aspiration, or RF ablation.

The device 120 may include first and second gears 122, 124 that rotate about axes of rotation 158, 160 that are not parallel to one another and that may not be perpendicular to one another. The third gear 200 rotates about a third axes of rotation 202 which is likewise not parallel to the axes or rotation 158, 160 and may not be perpendicular to the axes of rotation 158, 160. A fourth gear 204 is also present on the device 120 and rotates about a fourth gear axis of rotation 206 that is not parallel to any of the other axes of rotation 158, 160, 202. The fourth axes of rotation 206 may not be perpendicular to any of the other axes of rotation 158, 160 or 202. The four axes of rotation 158, 160, 202 and 206 may be arranged so that none of them are parallel to the catheter distal end longitudinal axis 184. The four gears 122, 124, 200, 204 may all be configured the same way having the same size and shape. The four gears 122, 124, 200 and 204 may be driven by their own individual torque transmission member 34 so that they can be independently controlled by the operator. In other arrangements, one or more of the four gears 122, 124, 200 and 204 can be linked to one another so that they are controlled by the same torque transmission member 34 and thus driven in sequence with one another. The housing 3 may be stationary with respect to the distal end 182 of the catheter 5, or may be capable of rotating 360 degrees relative to the catheter distal end longitudinal axis 184.

Figure 23:
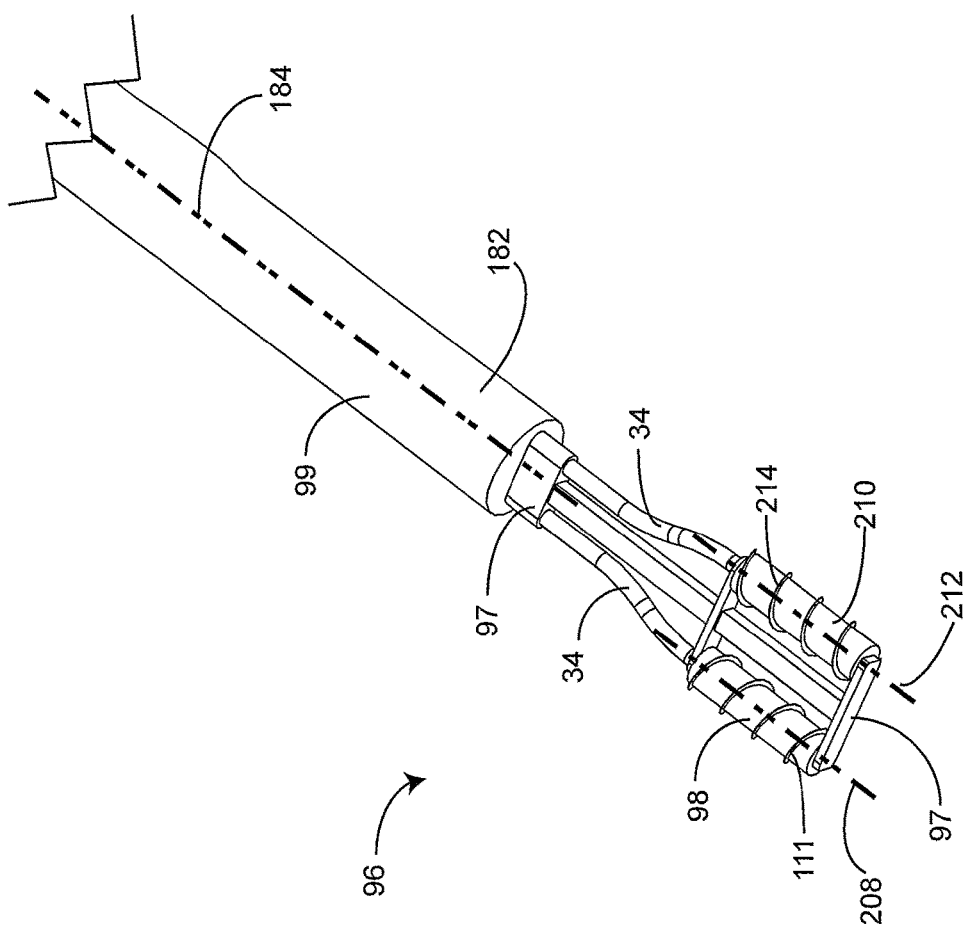
FIG. 23 is a perspective view of an embodiment which uses a screw-type mechanism.

FIG. 23 shows a screw-type end effector 96 embodiment allowing at least 2 degrees of freedom. The screw-type end effector 96 consists of cylindrical screw drives 98, 210 mounted to a frame 97. The cylindrical screw drives 98, 210 are attached to the frame 97 on their distal ends such that they can rotate freely about their longitudinal axes 208, 212. Attached to the proximal end of the cylindrical screw drives 98, 210 are torque transmission members 34. Extending proximally from the frame 97, the torque transmission members 34 are routed through a catheter 99. The frame 97 may be mounted to the distal end 182 of the catheter 99, and may extend such that the frame 97 is located both proximal and distal to both of the cylindrical screw drives 98, 210. The frame 97 is stationary with respect to the distal end 182 and does not move relative to the distal end 182.

The first cylindrical screw drive 98 may be provided with helical spines 111 thereon that are arranged so as to extend in the clockwise direction in the distal direction of the first cylindrical screw drive 98. The second cylindrical screw drive 210 may be provided with helical spines 214 that extend in the counter clockwise direction in the distal direction of the second cylindrical screw drive 210. The first cylindrical screw drive 98 has a first cylindrical screw drive axis of rotation 208 about which the first cylindrical screw drive 98 rotates, and the second cylindrical screw drive 210 has a second cylindrical screw drive axis of rotation 212 about which the second cylindrical screw drive 210 rotates. The axes of rotation 208 and 212 may be parallel to one another, and a portion of the frame 97 may or may not be disposed between the axes of rotation 208 and 212. Separate torque transmission members 34 may be used to control the cylindrical screw drives 98, 210 independently from one another, or in other arrangements the cylindrical screw drives 98, 210 could be driven by a single torque transmission member 34 and thus rotate in unison with one another at all times.

Driven in opposite rotational directions to one another, the helical spines 111, 214 on the cylindrical screw drives 98, 210 provide traction with the tissue 17 or media within which they are located, and propel the screw-type end effector 96 forward along its axis 184. Reverse the rotational direction of both cylindrical screw drives 98 and 210, and the screw-type end effector 96 will be propelled backwards along its axis 184. Driving both of the cylindrical screw drives 98 and 210 in the same direction will propel the screw-type end effector 96 laterally, or "left" and "right" and thus at a non-parallel angle to the axis 184. Besides a higher degree of freedom, the screw-type end effector 96 may be able to propel itself through fluids and semi-solids, as well as on the surfaces of tissues 17.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

REFERENCE LABELS

1 End Effector
2 Gear
3 Housing
4 Electrode
5 Catheter
6a Open Distance
6b Closed Distance
7 Slide Tubes
8 Slide Block
9 Sliding Catheter
10 Sliding Motion
11 Lumen Entrance
12 Lumen Exit
13 Exit Angle
14 Slide Lumen
15 Positive Charge
16 Ground
17 Tissue
18 Grasped Tissue
19 Area of Ablated Tissue
20 Central Electrode
21 Direction of Forward Motion
22 Flexible Electrode
23 Suction Lumen
24 Suction-based End Effector
25 Suction Port
26 Electrode
28 Housing
29 Catheter
30 Asymmetric End Effector
31 Asymmetric Housing
32 Passive Gear
33 Freewheeling Hub
34 Torque Transmission Member
35 Rotation Mechanism
36 Nested Path Slide Block
37 Nested Slide Lumen
38 Rotating Head End Effector
39 Rotating Head 40 Gripping Member
41 Stationary Housing
42 Handset
43 Power Wire Bundle
44 Outer Handset
45 Inner Handset
46 Drive Motor
47 Coupler
48 Slip Ring
49 Motor Power Wire
50 Ablation Switch Wire
51 Drive Switch Wire
52 Drive Switch
53 Ablation Switch
54 Sheath
55 Control Means
56 Inner Drive Gear
57 Outer Drive Gear
58 Gap
59 Inner Drive Gear Velocity
60 Outer Drive Gear Velocity
61 Inner Drive Path
62 Outer Drive Path
63 Rotation Radius
64 Rotation Pivot Point
65 Gear Tooth
66 Penetrating Point
67 Gear Tooth Shaft
68 Gear Tooth Base
69 Bore
70 Clip-on End Effector
71 Clip-on Housing
72 Housing Retention Clip
73 Distal End Cap
74 Functional Area
75 Angled Slider Plate
76 Retention Clip
77 Alignment Collar
78 Collar Bore
79 Endoscope
80 Medical Device with Clip-on End Effector
81 Angle Tooth Gear
82 Device with Side Mounted Gears
83 End Cap
84 Deflected Device with Side Mounted Gears
85 Deflection
86 Tooth Angle
87 Gear Base
88 Slider-type Mechanism
89 Console
90 Console Housing
91 Display Screen
92 Catheter Connection
93 Console Base
94 Control Knob
95 Control Button
96 Screw-type End Effector
97 Frame
98 First Cylindrical Screw Drive
99 Catheter
100 Endoscope Control Body
101 Control Body Handle
102 Control Body Retention Clip
103 Lightguide Tube
104 End Effector Control
105 Control Housing
106 Motor Control Button
107 Grip Control
108 Insertion Tube
109 Tooth
110 Meshing of Alternate Teeth
111 Helical Spine
112 Spacing
113 Tooth Profile Geometry
120 Device
122 First Gear
124 Second Gear
126 Spacing Mechanism
128 Spacing
130 First Slide Tube
132 Second Slide Tube
134 First Slide Lumen
136 Second Slide Lumen
142 Proximal End
144 Distal End
146 First Slide Lumen Entrance
148 First Slide Lumen Exit
150 Second Slide Lumen Entrance
152 Second Slide Lumen Exit
154 Distance
156 Distance
158 First Gear Axis of Rotation
160 Second Gear Axis of Rotation
162 Height
170 Gear Axis of Rotation
172 Radial Direction
174 Arc Length Direction
176 Upper Surface
178 Lower Surface
180 Outer Surface
182 Distal End
184 Catheter Distal End Longitudinal Axis
186 Second Gear Base
188 Second Gear Tooth Shaft
190 Second Gear Tooth Angle
192 Catheter Body
194 Catheter Body Longitudinal Axis
196 Rotation Mechanism Axis of Rotation
200 Third Gear
202 Third Gear Axis of Rotation
204 Fourth Gear
206 Fourth Gear Axis of Rotation
208 1st Cylindrical Screw Drive Axis of Rot.
210 Second Cylindrical Screw Drive
212 2nd Cylindrical Screw Drive Axis of Rot.
214 Helical Spines
216 Rotating Head Rotational Axis

What is claimed:

1. A device for gripping tissue having a longitudinal axis and a distal working end, said device comprising:
  first and second gears positioned adjacent to one another at said distal working end of said device and spaced apart from one another by a selected distance, said first and second gears configured to engage tissue in said distance therebetween;
  first and second members configured to provide rotational motion respectively to said first and second gears located respectively at distal ends of said first and second members;
  a user-controllable spacing mechanism associated with said first and second gears, said spacing mechanism selectively movable along said longitudinal axis of said device to adjust said first and second gears to any position between a first position having a maximum distance between said first and second gears and a second position having a minimum distance between said first and second gears, wherein selective adjustment of said user-controllable spacing mechanism along said longitudinal axis toward said distal working end decreases said distance between said first and second gears, and selective adjustment of said user-controllable spacing mechanism along said longitudinal axis away from said distal working end increases said distance between said first and second gears;

a mounting device configured to selectively affix said tissue gripping device to an endoscope, said first and second members extending through at least a portion of said mounting device when affixed to said endoscope;

said endoscope having:
(i) an endoscope control body including a control body handle, and
(ii) an end effector control having a control housing attached to said control body handle, said control housing having: (a) a user-actuated grip control lever operably coupled to at least one of said user-controllable spacing mechanism, said first member, and said second member to selectively adjust the spacing between said first and second gears, and (b) at least one user-actuated motor control button to selectively adjust torque transmission through the first and second members respectively to said first and second gears, wherein said end effector control is configured to control the rotation of at least one of said first and second gears.

2. The device as set forth in claim 1, wherein said spacing mechanism comprises:
a first slide tube, wherein said first gear is located on a distal end of said first slide tube;
a second slide tube, wherein said second gear is located on a distal end of said second slide tube;
a slide block defining first and second slide lumens therein, at least a portion of said first and second slide lumens extending in a curved direction through said slide block, and said first and second slide tubes positioned respectively in said first and second slide lumens.

3. The device as set forth in claim 2, further comprising:
an inner catheter having a distal end affixed to respective proximal ends of said first and second slide tubes; and
an outer catheter affixed to said slide block, said outer catheter coaxial with and exterior to said inner catheter, wherein movement of said outer catheter with respect to said inner catheter in the distal direction moves said slide block relative to said first and second slide tubes and moves said first and second gears toward said second position.

4. The device as set forth in claim 1, wherein said spacing mechanism includes a slide block having first and second slide lumens, wherein at least a portion of said first and second slide lumens extend in a curved direction through said slide block;
said first and second slide lumens having respective first and second slide lumen entrances located at a proximal end of said slide block, and respective first and second slide lumen exits located at a distal end of said slide block, wherein a distance between said first and second slide lumen entrances is shorter than a distance between said first and second slide lumen exits.

5. The device as set forth in claim 1, wherein said spacing mechanism includes a slide block having a proximal end, an opposite distal end, and first and second slide lumens extend from said proximal end to said distal end, said first and second slide lumens remaining separate from one another through said slide block, and said first slide lumen crossing said second slide lumen at a location between said proximal and distal ends of said slide block.

6. The device as set forth in claim 1, wherein said first gear is rotatable about a first gear axis of rotation and said second gear is rotatable about a second gear axis of rotation, wherein said first and second axes of rotation are oriented at an angle other than 180 degrees and 360 degrees relative to one another.

7. The device as set forth in claim 1, further comprising an electrode configured to contact said tissue and transfer electrical energy into said tissue, wherein said electrode is flexible and flexes relative to said first and second gears.

8. The device as set forth in claim 1, further comprising a suction port configured to apply a suction force to said tissue and urge said first and second gears toward said tissue.

9. The device as set forth in claim 1, wherein said first and second gears have teeth and wherein said teeth of said first gear mesh with said teeth of said second gear in said second position.

10. The device as set forth in claim 1, wherein said spacing mechanism includes a slide block having a proximal end, an opposite distal end, a height defined therebetween, and first and second slide lumens extending from said proximal end to said distal end, wherein paths of said first and second slide lumens through the slide block are nested and defined by the following equations:

$$x_c(h) = \frac{x_t + x_b}{\ln(|\cos(-\gamma)|)} \cdot \ln\left(\left|\cos\left(-\frac{h}{h_t}\gamma\right)\right|\right) - x_b$$

$$y_c(h) = -W(h) \cdot \frac{y_b}{2} \cdot \left[\cos\left(\frac{\pi h}{h_t}\right) + 1\right]$$

wherein: $x_c(h)$=center x-coordinate equation for nested slide lumen;
$y_c(h)$=center y-coordinate equation for nested slide lumen;
$x_t$=x-offset at top of slide block (distal end);
$x_b$=x-offset at bottom of slide block (proximal end);
$Y_b$=y-offset at bottom of slide block (proximal end);
$h_t$=height of slide block;
$W(h)$=weighting factor for shaping curvature (<0.05);
y=exit angle of slide path.

11. The device as set forth in claim 1, wherein said first-gear is rotatable about a first gear axis of rotation and said second gear is rotatable about a second gear axis of rotation, said each of said first and second gears having at least one gear tooth extending outwardly from said first and second gear axes of rotation in a radial direction, said at least one gear tooth including:
(i) a penetrating point located distal to said first or second gear axis of rotation and configured to penetrate tissue;
(ii) a gear tooth base located radially inwardly from said penetrating point and having a radially inwardly widening profile in an arc length direction, providing resistance to penetration of said penetrating point into said tissue; and
(iii) a gear tooth shaft extending between said penetrating point and said gear tooth base, said gear tooth shaft defining a penetration depth of said penetrating point.

12. The device as set forth in claim 11, wherein each of said first and second gears has a gear base extending radially inwardly from said gear tooth base and proximal to said first or second gear axis of rotation, said gear base having a width at least as wide as said gear tooth base in the arc length direction in the inward radial direction connecting said gear tooth shaft to said gear base, and wherein said penetrating point is contiguous with said gear tooth shaft, said gear tooth shaft is contiguous with said gear tooth base, and said gear tooth base is contiguous with said gear base.

13. The device as set forth in claim 11, wherein each of said first and second gears has from two to twelve gear teeth.

14. The device as set forth in claim 1, wherein said spacing mechanism is an angled slider plate selectively movable relative to an outer surface of said medical instrument between said first and second positions, said first and second members extending through said slider plate.

15. The device as set forth in claim 1, wherein said first and second members are selectively movable relative to an outer surface of said medical instrument; and wherein said spacing mechanism is an angled slider plate remaining stationary relative to said outer surface of said medical instrument, wherein said first and second members extend through the spacing mechanism and movement of said first and second members through said spacing mechanism adjusts said gears between said first and second positions.

16. The device as set forth in claim 1, wherein said mounting device is a clip-on housing having a housing retention clip configured to engage an outer surface of said medical instrument to selectively affix said clip-on housing to said medical instrument.

17. The device as set forth in claim 1, further comprising a retention clip that is selectively affixed to an outer surface of said medical instrument, wherein said retention clip is located proximal to said mounting device and said first and second members extend through said retention clip.

18. The device as recited in claim 1, further comprising a rotation mechanism having a rotation mechanism axis of rotation and capable of collectively rotating said first and second gears 360 degrees about said rotation mechanism axis of rotation.

19. A device for gripping tissue having a longitudinal axis and a distal working end, said device comprising:

first and second gears positioned adjacent to one another at said distal working end of said device and spaced apart from one another by a selected distance, said first and second gears configured to engage tissue in said distance therebetween;

first and second members configured to provide rotational motion respectively to said first and second gears located respectively at distal ends of said first and second members;

a user-controllable spacing mechanism associated with said first and second gears, said spacing mechanism selectively movable along said longitudinal axis of said device to adjust said first and second pears to any position between a first position having a maximum distance between said first and second gears and a second position having a minimum distance between said first and second gears, wherein selective adjustment of said user-controllable spacing mechanism along said longitudinal axis toward said distal working end decreases said distance between said first and second gears, and selective adjustment of said user-controllable spacing mechanism along said longitudinal axis away from said distal working end increases said distance between said first and second gears;

a mounting device configured to selectively affix said tissue gripping device to a medical instrument, said first and second members extending through at least a portion of said mounting device when affixed to said medical instrument;

a retention clip selectively affixed to an outer surface of said medical instrument, wherein said retention clip is located proximal to said mounting device and said first and second members extend through said retention clip; and an alignment collar proximal to said retention clip, wherein said first and second members extend through said alignment collar.

20. The device as set forth in claim 19, wherein said spacing mechanism comprises:

a first slide tube, wherein said first gear is located on a distal end of said first slide tube;

a second slide tube, wherein said second gear is located on a distal end of said second slide tube;

a slide block defining first and second slide lumens therein, at least a portion of said first and second slide lumens extending in a curved direction through said slide block, and said first and second slide tubes positioned respectively in said first and second slide lumens.

21. The device as set forth in claim 20, further comprising:

an inner catheter having a distal end affixed to respective proximal ends of said first and second slide tubes; and an outer catheter affixed to said slide block, said outer catheter coaxial with and exterior to said inner catheter, wherein movement of said outer catheter with respect to said inner catheter in the distal direction moves said slide block relative to said first and second slide tubes and moves said first and second gears toward said second position.

22. The device as set forth in claim 19, wherein said spacing mechanism includes a slide block having first and second slide lumens, wherein at least a portion of said first and second slide lumens extend in a curved direction through said slide block;

said first and second slide lumens having respective first and second slide lumen entrances located at a proximal end of said slide block, and respective first and second slide lumen exits located at a distal end of said slide block, wherein a distance between said first and second slide lumen entrances is shorter than a distance between said first and second slide lumen exits.

23. The device as set forth in claim 19, wherein said spacing mechanism includes a slide block having a proximal end, an opposite distal end, and first and second slide lumens extend from said proximal end to said distal end, said first and second slide lumens remaining separate from one another through said slide block, and said first slide lumen crossing said second slide lumen at a location between said proximal and distal ends of said slide block.

24. The device as set forth in claim 19, wherein said first ear is rotatable about a first gear axis of rotation and said second gear is rotatable about a second gear axis of rotation, wherein said first and second axes of rotation are oriented at an angle other than 180 degrees and 360 degrees relative to one another.

25. The device as set forth in claim 19, further comprising an electrode configured to contact said tissue and transfer electrical energy into said tissue, wherein said electrode is flexible and flexes relative to said first and second gears.

26. The device as set forth in claim 19, further comprising a suction port configured to apply a suction force to said tissue and urge said first and second gears toward said tissue.

27. The device as set forth in claim 19, wherein said first and second gears have teeth and wherein said teeth of said first gear mesh with said teeth of said second gear in said second position.

28. The device as set forth in claim 19, wherein said spacing mechanism includes a slide block having a proximal end, an opposite distal end, a height defined therebetween, and first and second slide lumens extending from said proximal end to said distal end, wherein paths of said first and second slide lumens through the slide block are nested and defined by the following equations:

$$x_c(h) = \frac{x_t + x_b}{\ln(|\cos(-\gamma)|)} \cdot \ln\left(\left|\cos\left(-\frac{h}{h_t}\gamma\right)\right|\right) - x_b$$

$$y_c(h) = -W(h) \cdot \frac{y_b}{2} \cdot \left[\cos\left(\frac{\pi h}{h_t}\right) + 1\right]$$

wherein: $x_c(h)$=center x-coordinate equation for nested slide lumen;
$Y_c(h)$=center y-coordinate equation for nested slide lumen;
$x_t$=x-offset at top of slide block (distal end);
$x_b$=x-offset at bottom of slide block (proximal end);
$y_b$=y-offset at bottom of slide block (proximal end)
$h_t$=height of slide block;
$W(h)$=weighting factor for shaping curvature (<0.05);
$\gamma$=exit angle of slide path.

29. The device as set forth in claim 19, wherein said first gears is rotatable about a first gear axis of rotation and a second gear is rotatable about a second axis of rotation, each of said first and second gears having at least one gear tooth extending outwardly from said first and second gear axes of rotation in a radial direction, said at least one gear tooth including:
(i) a penetrating point located distal to said first and second gear axis of rotation and configured to penetrate tissue;
(ii) a gear tooth base located radially inwardly from said penetrating point and having a radially inwardly widening profile in an arc length direction, providing resistance to penetration of said penetrating point into said tissue; and
(iii) a gear tooth shaft extending between said penetrating point and said gear tooth base, said gear tooth shaft defining a penetration depth of said penetrating point.

30. The device as set forth in claim 29, wherein each of said first and second gears has a gear base extending radially inwardly from said gear tooth base and proximal to said first or second gear axis of rotation, said gear base having a width at least as wide as said gear tooth base in the arc length direction in the inward radial direction connecting said gear tooth shaft to said gear base, and
wherein said penetrating point is contiguous with said gear tooth shaft, said gear tooth shaft is contiguous with said gear tooth base, and said gear tooth base is contiguous with said gear base.

31. The device as set forth in claim 29, wherein each of said first and second gears has from two to twelve gear teeth.

32. The device as set forth in claim 19, wherein said medical instrument is an endoscope.

33. The device as set forth in claim 32, wherein said endoscope has an endoscope control body and an end effector control attached to said endoscope control body, wherein said end effector control controls the rotation of at least one of said first and second gears.

34. The device as set forth in claim 33, wherein said endoscope control body includes a control body handle, and said end effector control has a control housing attached to said control body handle and includes:
(i) a user-actuated grip control lever operably coupled to at least one of said user-controllable spacing mechanism, said first member, and said second member to selectively adjust the spacing between said first and second gears, and
(ii) at least one user-actuated motor control button to selectively adjust torque transmission through the first and second members respectively to said first and second gears.

35. The device as set forth in claim 19, wherein said spacing mechanism is an angled slider plate selectively movable relative to an outer surface of said medical instrument between said first and second positions, said first and second members extending through said slider plate.

36. The device as set forth in claim 19, wherein said first and second members are selectively movable relative to an outer surface of said medical instrument; and
wherein said spacing mechanism is an angled slider plate remaining stationary relative to said outer surface of said medical instrument, wherein said first and second members extend through the spacing mechanism and movement of said first and second members through said spacing mechanism adjusts said gears between said first and second positions.

37. The device as set forth in claim 19, wherein said mounting device is a clip-on housing having a housing retention clip configured to engage an outer surface of said medical instrument to selectively affix said clip-on housing to said medical instrument.

38. The device as recited in claim 19, further comprising a rotation mechanism having a rotation mechanism axis of rotation and ca able of collectively rotating said first and second gears 360 degrees about said rotation mechanism axis of rotation.

* * * * *